US010596267B2

(12) United States Patent
Borenstein et al.

(10) Patent No.: US 10,596,267 B2
(45) Date of Patent: Mar. 24, 2020

(54) METHOD AND PROCESS FOR QUANTITATIVE EVALUATION OF PHARMACOKINETICS, THERAPEUTIC EFFECTS AND SAFETY OF DELIVERY OF DRUG COMPOUNDS TO THE INNER EAR FOR TREATMENT OF AUDITORY DISEASE

(71) Applicants: The Charles Stark Draper Laboratory, Inc., Cambridge, MA (US); Massachusetts Eye and Ear Infirmary, Boston, MA (US); Massachusetts Institute of Technology, Cambridge, MA (US)

(72) Inventors: Jeffrey T. Borenstein, Newton, MA (US); Erin Pararas, Swampscott, MA (US); Ernest S. Kim, Cambridge, MA (US); Vishal Tandon, Cambridge, MA (US); Andrew Ayoob, Cambridge, MA (US); Michael McKenna, Boston, MA (US); William Sewell, Boston, MA (US); Marcello Peppi, Cambridge, MA (US); Marc Weinberg, Needham, MA (US); Robert Langer, Cambridge, MA (US)

(73) Assignees: The Charles Stark Draper Laboratory, Inc., Cambridge, MA (US); Massachusetts Eye and Ear Infirmary, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/631,933

(22) Filed: Jun. 23, 2017

(65) Prior Publication Data
US 2018/0000956 A1 Jan. 4, 2018

Related U.S. Application Data

(60) Provisional application No. 62/353,676, filed on Jun. 23, 2016.

(51) Int. Cl.
| | | |
|---|---|---|
| *A61K 9/00* | (2006.01) | |
| *A61K 9/06* | (2006.01) | |
| *A61K 47/10* | (2017.01) | |
| *A61K 47/60* | (2017.01) | |
| *A61K 31/498* | (2006.01) | |

(52) U.S. Cl.
CPC .......... *A61K 47/60* (2017.08); *A61K 9/0046* (2013.01); *A61K 9/06* (2013.01); *A61K 31/498* (2013.01); *A61K 47/10* (2013.01)

(58) Field of Classification Search
CPC ....... A61K 47/10; A61K 9/0046; A61L 27/50; A61L 27/52; A61L 27/54
See application file for complete search history.

(56) References Cited

U.S. PATENT DOCUMENTS

| | | | |
|---|---|---|---|
| 8,099,156 B1 * | 1/2012 | Schnitzer | A61B 1/043 600/476 |
| 2010/0015263 A1 | 1/2010 | Lichter et al. | |
| 2013/0085476 A1 | 4/2013 | Imran | |
| 2014/0200395 A1 | 7/2014 | Shafi et al. | |
| 2015/0359927 A1 * | 12/2015 | Bennett | A61K 9/06 424/422 |

OTHER PUBLICATIONS

Hutten et al. (PLOS One, Aug. 2014, vol. 9, pp. 1-13) (Year: 2014).*
Yu et al (International Journal of Pharmaceutics, online Apr. 2014, vol. 470, pp. 151-157) (Year: 2014).*
Sutton (The Surgical Technologist, Ear Surgery—An Overview, 2007, pp. 61-66) (Year: 2007).*
El Kechai Naila et al: "Recent advances in local drug delivery to the inner ear", International Journal of Pharmaceutics, vol. 494, No. 1 , pp. 83-101.
International Search Report and Written Opinion for PCT/US2017/039090 dated Sep. 22, 2017.
Yu Dehong et al: "Inner ear delivery of dexamethasone using injectable silk-polyethylene glycol (PEG) hydrogel", International Journal of Pharmaceutics, Elsevier, Amsterdam, NL, vol. 503, No. 1, Mar. 10, 2016 (Mar. 10, 2016), pp. 229-237.
Yu Jing et al: "In situ covalently cross-linked PEG hydrogel for ocular drug delivery applications", International Journal of Pharmaceutics, vol. 470, No. 1 , pp. 151-157.
Mao-li, Duan et al., "Permeability of round window membrane and its role for drug delivery: our own findings and literature review," Journal of Otology, 2009, vol. 4, No. 1, pp. 34-43.
International Preliminary Report on Patentability for PCT/US2017/039090 dated Jan. 3, 2019.

* cited by examiner

*Primary Examiner* — Mark V Stevens
(74) *Attorney, Agent, or Firm* — Christopher J. McKenna; Foley & Lardner LLP

(57) ABSTRACT

The present disclosure provides compositions and methods for treating an auditory disease in a subject in need thereof comprising administering an effective amount of a gel-based precursor that includes an inner ear-specific therapeutic compound directly into the cochlea of the subject.

18 Claims, 10 Drawing Sheets

With binding reactions, $v_0 = 4.1\ \mu M$

With binding reactions, $v_0 = 41\ \mu M$

Slice 8/30  Slice 9/30  Slice 10/30  Slice 11/30
Slice 12/30  Slice 13/30  Slice 14/30  Slice 15/30

METHOD AND PROCESS FOR QUANTITATIVE EVALUATION OF PHARMACOKINETICS, THERAPEUTIC EFFECTS AND SAFETY OF DELIVERY OF DRUG COMPOUNDS TO THE INNER EAR FOR TREATMENT OF AUDITORY DISEASE

CROSS-REFERENCE TO RELATED APPLICATIONS

This application claims the benefit of and priority to U.S. Application No. 62/353,676, filed Jun. 23, 2016, the contents of which are incorporated herein by reference in their entireties.

STATEMENT OF GOVERNMENT SUPPORT

This invention was made with government support under R01 DC006848-01A2, awarded by the National Institutes of Health. The government has certain rights in the invention.

TECHNICAL FIELD

The present technology relates generally to compositions and methods for treating an auditory disease in a subject in need thereof. In some embodiments, the methods comprise administering an effective amount of a gel-based precursor comprising an inner ear-specific therapeutic compound directly into the cochlea of the subject.

BACKGROUND

The following description of the background of the present technology is provided simply as an aid in understanding the present technology and is not admitted to describe or constitute prior art to the present technology.

Disorders of the inner ear comprise the largest and most serious class of diseases responsible for hearing loss, with 250 million people worldwide suffering from disabling hearing loss (Holley M C, *Drug Discov Today* 10(19):1269-82 (2005)). In the United States alone, 28 million patients suffer from sensorineural hearing loss (SNHL), a condition that currently causes an irreversible decline in cochlear function, and profound deafness remains the most prevalent serious medical condition at birth, with 3 in 1000 newborns suffering from this condition. In addition to these auditory disorders, tinnitus remains an intractable problem for many patients.

The principal challenge in treatment of inner ear diseases remains the inaccessibility of targets for therapy, due largely to the presence of the blood-cochlear barrier. Oral medications are typically blocked by the blood-cochlear barrier. Intratympanic delivery of compounds for treatment of inner ear diseases relies upon diffusion through the round window membrane (RWM), a structure with widely disparate transport properties depending upon the patient and disease state. This variability results in poor dosage control, and coupled with the reliance on passive diffusion mechanisms to transport drugs along the length of the cochlea, has limited the effectiveness of intratympanic delivery. See Borenstein J., *Expert Opin Drug Deliv.* 8(9):1161-1174 (2011).

SUMMARY OF THE PRESENT TECHNOLOGY

In an aspect, a hydrogel kit is provided which includes a first composition (a first "pack" composition) that includes about 10 wt. % to about 50 wt. % by weight of the first composition of a PEG thiol, a PEG thiol-ester, or a mixture thereof; and water. The hydrogel kit also includes a second composition (a second "pack" composition), where the second composition includes about 10 wt. % to about 50 wt. % by weight of the second pack composition of a PEG Michael acceptor; and water. In any embodiment of the hydrogel kit, it may be at least the PEG thiol, PEG thiol-ester, or mixture thereof includes one or more of a multi-arm PEG thiol, a multi-arm PEG thiol-ester, or a mixture thereof. In any embodiment of the hydrogel kit, it may be at least the Michael acceptor includes a multi-arm Michael acceptor.

In one aspect, the present disclosure provides a method for treating an auditory disease in a subject in need thereof comprising administering an effective amount of a first pack composition and an effective amount of a second pack composition to the subject, wherein (a) the first pack composition comprises about 10 wt. % to about 50 wt. % by weight of the first pack composition of a PEG thiol, a PEG thiol-ester, or a mixture thereof; and water; (b) the second pack composition comprises about 10 wt. % to about 50 wt. % by weight of the second pack composition of a PEG Michael acceptor; and water; and (c) the first pack composition and/or the second pack composition further comprises at least one inner ear-specific therapeutic agent, wherein the first pack composition and/or the second pack composition is administered through a cannula that penetrates the round window membrane of the subject. In any embodiment of the method for treating an auditory disease, it may be at least the PEG thiol, PEG thiol-ester, or mixture thereof includes one or more of a multi-arm PEG thiol, a multi-arm PEG thiol-ester, or a mixture thereof. In any embodiment of the method for treating an auditory disease, it may be at least the Michael acceptor includes a multi-arm Michael acceptor.

In another aspect, the present disclosure provides a method for treating an auditory disease in a subject in need thereof comprising administering an effective amount of a first pack composition and an effective amount of a second pack composition to the subject, wherein (a) the first pack composition comprises about 10 wt. % to about 50 wt. % by weight of the first pack composition of a PEG thiol, a PEG thiol-ester, or a mixture thereof; and water; (b) the second pack composition comprises about 10 wt. % to about 50 wt. % by weight of the second pack composition of a PEG Michael acceptor; and water; and (c) the first pack composition and/or the second pack composition further comprises at least one inner ear-specific therapeutic agent, wherein the first pack composition and/or the second pack composition is administered through a cannula that accesses a cochleostomy site or a canalostomy site in the inner ear of the subject. In any embodiment of the method, it may be at least the PEG thiol, PEG thiol-ester, or mixture thereof includes one or more of a multi-arm PEG thiol, a multi-arm PEG thiol-ester, or a mixture thereof. In any embodiment of the method, it may be at least the Michael acceptor includes a multi-arm Michael acceptor. In some embodiments, the cochleostomy site is located within the cochlear bone of the subject. In certain embodiments, the canalostomy site is located within the semicircular canals of the subject. Additionally or alternatively, in some embodiments, the method further comprises resealing the cannula with sodium hyaluronate, a muscle graft, a fat graft, or a fascia graft.

In any of the above embodiments of the methods disclosed herein, a microfluidic tubing or a high-gauge needle is used to infuse the first pack composition and/or the second pack composition through the cannula. In certain embodiments, the first pack composition and/or the second pack composition is administered into a fluid-filled cochlear tube selected from the group consisting of scala tympani (ST), scala vestibuli, and scala media. In any of the above embodiments of the methods disclosed herein, the first pack composition and/or the second pack composition form a hydrogel in situ having an elastic modulus between 1 and 1,000 kPa.

Additionally or alternatively, in some embodiments of the methods disclosed herein, the at least one inner ear-specific therapeutic agent comprises a corticosteroid, an aminoglycoside, a free radical scavenger agent, a small peptide therapeutic, a gene therapy related agent, or a combination of any two or more thereof. The at least one inner ear-specific therapeutic agent may comprise ciprofloxacin, gacyclidine, a γ-secretase inhibitor, dexamethasone, hydrocortisone, methylprednisolone, prednisolone, gentamicin, amikacin, streptomycin, neomycin, tobramycin, N-acetylcysteine (NAC), methionine, tocopherol, vitamin E, ebselen, tiopronin, organic thiophosphate, copper compounds, an inhibitor for glycogen synthase kinase-3 beta (GSK3β), valproic acid, a TGF-β inhibitor, epidermal growth factor, basic fibroblast growth factor, insulin like growth factor 1, neurotrophin-3 (NT-3), an agonist for the GDNF receptor (e.g., XIB4035), brain derived neurotrophic factor, a lipid vector, a viral vector, a non-viral vector, a polyplex, a liposome, a microsome, a polymersome, a lioplex, an oligonucleotide, naked DNA, small RNA, CRISP-Cas9, or a combination of any two or more thereof.

Additionally or alternatively, in some embodiments of the methods disclosed herein, the first pack composition and the second pack composition are administered simultaneously or sequentially. The first pack composition and/or the second pack composition may be administered as a single injection or multiple injections. In some embodiments of methods of the present technology, the subject is human.

Additionally or alternatively, in some embodiments of the methods disclosed herein, the first pack composition and/or the second pack composition further comprises a fluorescent tracer compound. The fluorescent tracer compound may be selected from the group consisting of FM 1-43 FX, GTTR, Phalloidin, Hoechst, Mitotracker, Q-tracker, and CFSE.

In any of the above embodiments of the methods disclosed herein, the auditory disease is selected from the group consisting of sensorineural hearing loss, noise-induced hearing loss, sudden sensorineural hearing loss, autoimmune inner ear disease, tinnitus, cisplatin ototoxicity protection, radiation-induced ototoxicity protection, Meniere's disease, and cranial nerve schwannoma. In certain embodiments of the methods, the administration of the first pack composition and/or the second pack composition results in an increase in survival and/or regeneration of inner hair cells or outer hair cells. Additionally or alternatively, in some embodiments of the methods disclosed herein, the administration of the first pack composition and/or the second pack composition results in an improvement of one or more electrophysiological parameters selected from the group consisting of Auditory Brainstem Response, Compound Action Potential, hearing thresholds, and Distortion Product Optoacoustic Emissions relative to that observed in an untreated control subject having auditory disease.

BRIEF DESCRIPTION OF THE DRAWINGS

FIG. 1(a) is a schematic of click chemistry and the Thiol-Type Michael Addition Mechanism. FIG. 1(b) shows multifunctional poly(ethylene glycol) oligomers with various click reactive functional groups. FIG. 1(c) shows the dynamic rheology plots showing evolution of hydrogel network formation: G' (storage modulus) and G" (loss modulus) at 4° C., 25° C., and 37° C. FIG. 1(d) shows a hydrogel formed after injection into a capillary tube at 4° C.

FIG. 2(a) shows the steps involved in one complete cycle of a reciprocating delivery scheme, along with the computational approach used. Pharmacokinetics are modeled using a pseudo-1D diffusion-reaction equation, where changes in the cross-sectional area of the cochlea as a function of position are considered, as well as drug binding to proteins. Pump-mediated convective infusion or extraction of a bolus of fluid is treated as instantaneous, owing to the short time constant of the system (on the order of seconds) as compared to the long diffusion times (thousands of seconds) considered. FIG. 2(b) shows the cross-sectional area of the cochlea as a function of position. FIG. 2(c) shows the drug concentration as a function of position in the cochlea after 4 cycles of reciprocating delivery. For each cycle, 1 μL of drug was infused 4.8 mm from the base of the cochlea, allowed to diffuse for 9,900 s, and then 1 μL of fluid was extracted from the cochlea. 100 s of diffusion after extraction was also modeled. FIG. 2(d) shows the drug concentration as a function of position after each step in the reciprocating delivery scheme. FIG. 2(e) shows the drug concentration as a function of time at several positions in the cochlea, corresponding to characteristic frequencies of 32, 24, 16, 12, 8, 5.6, 4, and 2.78 kHz.

FIG. 3(a) shows distortion product optoacoustic emissions (DPOAE; dashed lines, open circles) and compound action potential (CAP; solid lines, closed circles) threshold shifts as a function of time during infusion of artificial perilymph (control) and DNQX (an AMPA receptor blocker that disrupts afferent synaptic transmission of auditory signals) into guinea pig *cochleae* using a micropump. Infusion began at t=0. A hearing threshold is the minimum sound pressure level (measured in dB SPL) required to generate a response. Data reported are threshold shifts, the change in threshold as compared to baseline. FIG. 3(b) shows the same data presented in FIG. 3(a) in heat map form, indicating the spreading and distribution of the DNQX. CAP amplitudes are also shown, with a legend that is on a log scale.

FIG. 5(a) shows the intensity vs. concentration calibration curve for sodium fluorescein standards on a Zeiss LSM 710 confocal microscope. Because confocal microscopes are designed to be very sensitive within a narrow dynamic range, careful calibrations are necessary to quantitatively evaluate fluorescent histological sections. FIG. 5(b) shows guinea pig cochlea dissected into whole-mount sections for analysis. FIG. 5(c) shows several slices of a confocal z-stack image showing fluorescent staining of hair cells 3 hours after delivery of FM 1-43 FX. Tissue was fixed 3 hours after intracochlear delivery of 2 µL of 35 µM FM 1-43 FX in artificial perilymph. The darker areas indicate brighter fluorescence. FIG. 5(d) shows the fluorescence intensity along the inner hair cells as a function of distance from the apex, 3 hours after injection of FM 1-43 at the base of the cochlea.

DETAILED DESCRIPTION

Figures 1A, 1B:
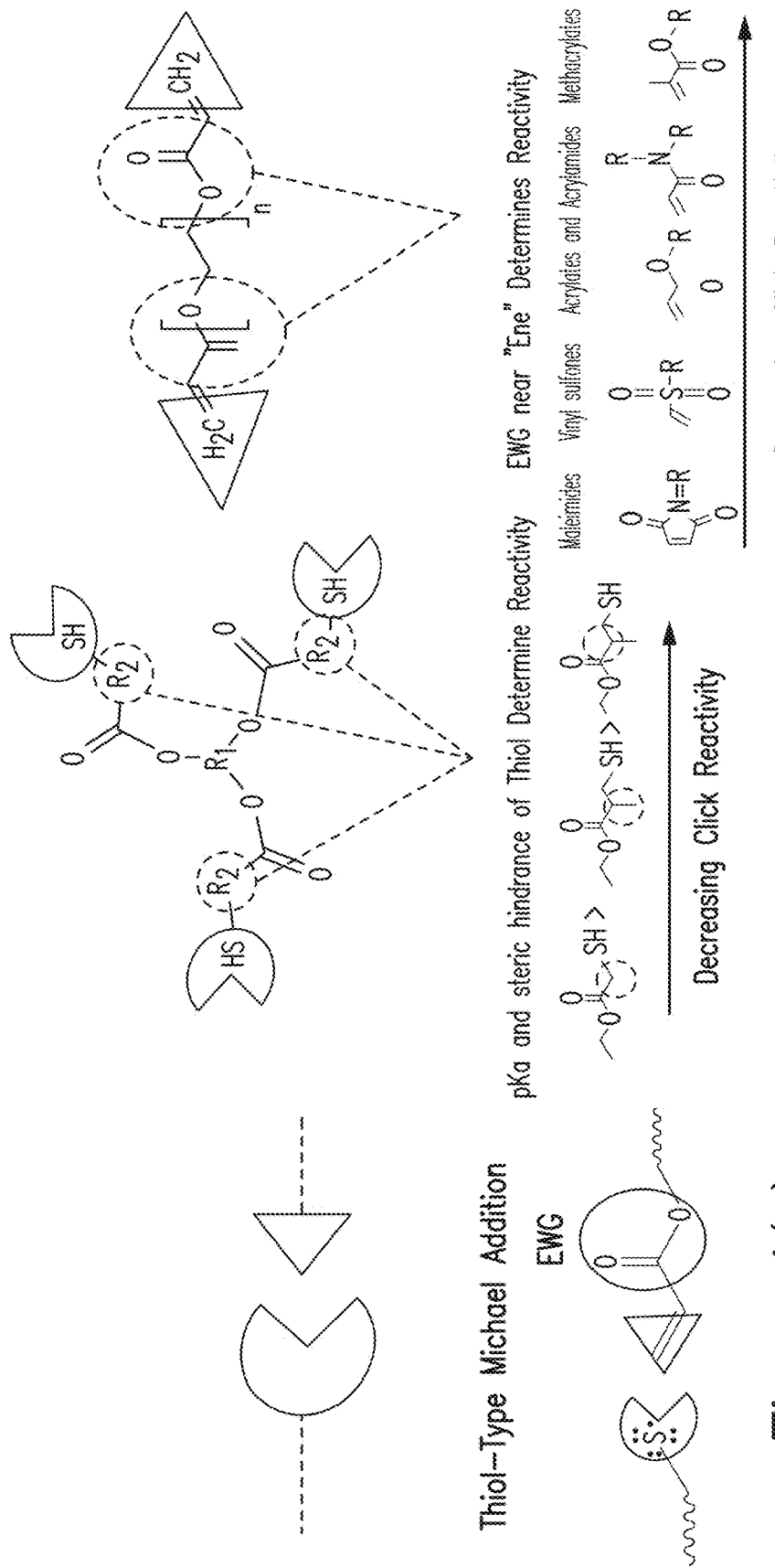
FIG. 1(a), FIG. 1(b), FIG. 1(c) and FIG. 1(d) show the chemical design and projected delivery kinetics of a biodegradable gel designed to be administered directly into the cochlear fluids of a subject that suffers from hearing loss or auditory disease.

It is to be appreciated that certain aspects, modes, embodiments, variations and features of the present methods are described below in various levels of detail in order to provide a substantial understanding of the present technology.

Assessment of pharmacokinetics and pharmacodynamics are critical aspects of the development of drug delivery systems (Salt A N & Plontke S K, *Audiol Neurootol.* 14(6):350-60 (2009)). Establishing intracochlear delivery methods with optimal pharmacokinetic profiles can be challenging because of the remoteness and small size of hearing structures, and difficulties in imaging drug transport. An additional requirement of inner ear drug delivery applications is the preservation of hearing structures and minimization of surgical trauma.

Provided herein are methods and processes for evaluating the pharmacokinetics, therapeutic efficacy, and safety of drugs designed to treat auditory diseases and/or hearing loss in a subject in need thereof. The methods of the present technology overcome many uncertainties associated with current drug delivery techniques to the inner ear. These obstacles are principally associated with drug transport through intervening tissues and structures between the delivery site and the target site. The methods of the present technology provide a higher degree of reliability and precision in terms of drug transport/concentration and permit a quantitative evaluation of drug safety and efficacy.

In one aspect, the present technology provides a method for directly accessing the cochlea of a subject in need thereof in a minimally invasive manner comprising administering to the subject an effective amount of gel precursor solutions including an inner ear-specific therapeutic agent, wherein the gel precursor solutions are administered through a cannula that accesses a cochleostomy site or a canalostomy site in the inner ear of the subject, and the cannula is sealed/removed after the gel-based precursor solutions are delivered. Alternatively, the cochlea may be accessed by administering to the subject an effective amount of gel precursor solutions including an inner ear-specific therapeutic agent, wherein the gel precursor solutions are administered through a cannula that penetrates the round window membrane (RWM) temporarily. Drug release and diffusion across the cochlear structures occurs over a period of time following drug delivery. Experimental and computational approaches for modeling drug pharmacokinetics and evaluating the effects of a therapeutic drug on hearing and on cell/tissue structures are also described herein.

Definitions

Unless defined otherwise, all technical and scientific terms used herein generally have the same meaning as commonly understood by one of ordinary skill in the art to which this technology belongs. As used in this specification and the appended claims, the singular forms "a", "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

As used herein, the "administration" of an agent or drug to a subject includes any suitable route of introducing or delivering to a subject a compound to perform its intended function. Administration includes self-administration and the administration by another.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a compound or composition known to exhibit the desired therapeutic effect) and a negative control (a subject or a sample that does not receive the therapy or receives a placebo) are typically employed.

As used herein, the term "effective amount" refers to a quantity sufficient to achieve a desired therapeutic and/or prophylactic effect, e.g., an amount which results in the prevention of, or a decrease in a disease or condition described herein or one or more symptoms or signs associated with a disease or condition described herein. In the context of therapeutic or prophylactic applications, the amount of a composition administered to the subject will vary depending on the composition, the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compositions may be administered to a subject having one or more signs or symptoms of a disease or condition described herein. As used herein, a "therapeutically effective amount" of a composition refers to composition levels in which the physiological effects of a disease or condition are ameliorated or eliminated. A therapeutically effective amount can be given in one or more administrations.

As used herein, the term "therapeutic agent" is intended to mean a compound that, when present in an effective amount, produces a desired therapeutic effect on a subject in need thereof.

As used herein, the terms "subject", "individual", or "patient" can be an individual organism, a vertebrate, a mammal, or a human. In some embodiments, the individual, patient, or subject is a human.

"Treating" or "treatment" as used herein covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments, treatment means that the symptoms associated with the disease are, e.g., alleviated, reduced, cured, or placed in a state of remission.

It is also to be appreciated that the various modes of treatment of diseases as described herein are intended to mean "substantial," which includes total but also less than total treatment, and wherein some biologically or medically relevant result is achieved. The treatment may be a continuous prolonged treatment for a chronic disease or a single, or few time administrations for the treatment of an acute condition.

Inner Ear Diseases

The cochlea (the hearing organ) resides along with the vestibular organ in the inner ear, and is responsible for converting mechanical signals from the middle ear into electrical signals that are transmitted along the auditory nerve toward the brainstem. Direct drug delivery to the organ is difficult on account of its small size and remote location. The cochlea, roughly 32 mm in length in humans, comprises three coiled fluid-filled tubes, the scala tympani (ST), scala vestibuli, and scala media. The ST terminates at the round window membrane (RWM). The scala vestibuli terminates at the oval window, which houses the stapes or footplate that transmits mechanical signals from the middle ear. The scala vestibuli and tympani connect to each other at the apex of the cochlea via the helicotrema. Sound from the outer ear causes motion of the eardrum or tympanic membrane, which in turn generates motion of the fluids in the inner ear. The cochlea contains the Organ of Corti (OC), which comprises three rows of outer hair cells (OHC) and one row of inner hair cells (IHC) along a basilar membrane. The IHCs respond to the waveform of a sound stimulus by releasing neurotransmitters to activate auditory nerve fibers. Loss of function of the hair cells and auditory neurons result in hearing loss.

The two principal fluids present in the cochlea are perilymph and endolymph. Perilymph is in direct contact with the basolateral surface of the hair cells and auditory neurons. Endolymph, the fluid contained within the scala media, bathes the apical surface of hair cells and has an ionic composition similar to the intracellular fluid environment. The cochlea contains a highly vascularized region known as the stria vascularis that maintains a unique electrochemical environment that supports transduction of sound by the IHC.

Functional assessment of hearing utilizes a well-established set of electrophysiological parameters with known effects on specific hearing structures. These include Distortion Product OtoAcoustic Emissions (DPOAE) and the Auditory Brainstem Response (ABR). In addition, Compound Action Potential (CAP) measurements are often used in drug delivery experiments to evaluate delivery kinetics. Each of these can be assessed at specific frequencies; the tonotopic arrangement of the cochlea provides a spatial map of hair cell function due to the correlation between particular frequency response and position along the length of the cochlea. Measurement of DPOAE is accomplished by introducing two tone pips with predetermined sound levels and frequencies into the ear canal; the inner ear generates acoustic emissions as a result of mechanical motion of the basilar membrane that provide a direct assessment of the function of the OHC. One particularly useful application of DPOAE measurements in drug delivery experiments is as a baseline measurement to assess surgically-induced trauma. The CAP measurement is a far-field electrocochleographic technique that monitors nerve fiber response to tone pips, often by using a ball electrode positioned in the vicinity of the RWM. This technique can be used as a measure of cochlear function at specific frequencies, providing a map of hair cell function through the cochlea during drug delivery experiments.

Gel Compositions

In an aspect, a hydrogel kit is provided which includes a first composition (a first "pack" composition) that includes about 10 wt. % to about 50 wt. % by weight of the first composition of a PEG thiol, a PEG thiol-ester, or a mixture thereof; and water. The hydrogel kit also includes a second composition (a second "pack" composition), where the second composition includes about 10 wt. % to about 50 wt. % by weight of the second pack composition of a PEG Michael acceptor; and water.

The amount of PEG thiol, PEG thiol-ester, or mixture thereof (of any embodiment herein included) in the first composition (by weight of the first composition) may be about 10 wt. %, about 12 wt. %, about 14 wt. %, about 16 wt. %, about 18 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, or any range including and/or in between any two of these values.

The PEG thiol may be a linear PEG thiol, a multi-arm PEG thiol, or a mixture thereof. Scheme 1 provides an illustrative representation of a linear PEG thiol and a type of multi-arm PEG thiol (specifically, a 3-arm PEG thiol), where n, m, p, and q are each independently integers greater than 1. $X^1$ is a core of the multi-arm PEG, such as e.g., glycerol for a 3-arm PEG thiol, although other cores may be used for a 3-arm PEG scaffolds to provide a 3-arm PEG thiol. Similarly, the appropriate core provides, e.g., 4-arm, 6-arm, and 8-arm PEG scaffolds, such as (but not limited to) pentaerythritol for 4-arm PEG scaffolds, dipentaerythritol for 6-arm PEG scaffolds, and tripentaerythritol and/or hexaglycerol for 8-arm PEG scaffolds. Thus, the multi-arm PEG thiol may be a 3-arm PEG thiol, a 4-arm PEG thiol, a 6-arm PEG thiol, and 8-arm PEG thiol, or a mixture of any two or more thereof.

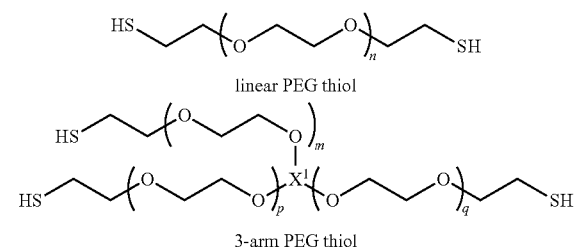

Scheme 1.

linear PEG thiol 3-arm PEG thiol

Similarly, the PEG thiol-ester may be a linear PEG thiol-ester, a multi-arm PEG thiol-ester, or a mixture thereof. Scheme 2 provides an illustrative representation of a linear PEG thiol-ester and a type of multi-arm PEG thiol-ester (here, a 3-arm PEG thiol-ester), where n', p', and q' are each independently integers greater than 1, $X^2$ is a core of the multi-arm PEG, and $R^1$, $R^2$, $R^3$, $R^4$, $R^5$, $R^6$, $R^7$, $R^8$, $R^9$, and $R^{10}$ are each independently H or methyl.

Scheme 2.

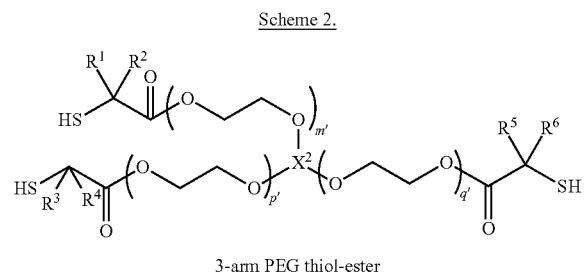

3-arm PEG thiol-ester

PEG Michael acceptor, a 6-arm PEG Michael acceptor, 8-arm PEG Michael acceptor, or a mixture of any two or more thereof.

In any embodiment herein, the PEG Michael acceptor (whether a linear PEG Michael acceptor, a multi-arm PEG Michael acceptor, or a mixture thereof) may be a PEG maleimide, a PEG vinyl sulfone, a PEG acrylate, a PEG arylamide, a PEG methacrylate, or a mixture of any two or more thereof. Merely by way of illustration, Scheme 3 provides a representation of a linear PEG maleimide, a linear PEG vinyl sulfone, a linear PEG acrylate, a linear PEG arylamide, and a linear PEG methacrylate. In Scheme 3, a, b, c, d, and e are each independently integers greater than 1, and $R^{11}$ and $R^{12}$ are each independently H or an alkyl group such as methyl, ethyl, n-propyl, or i-propyl.

Scheme 3.

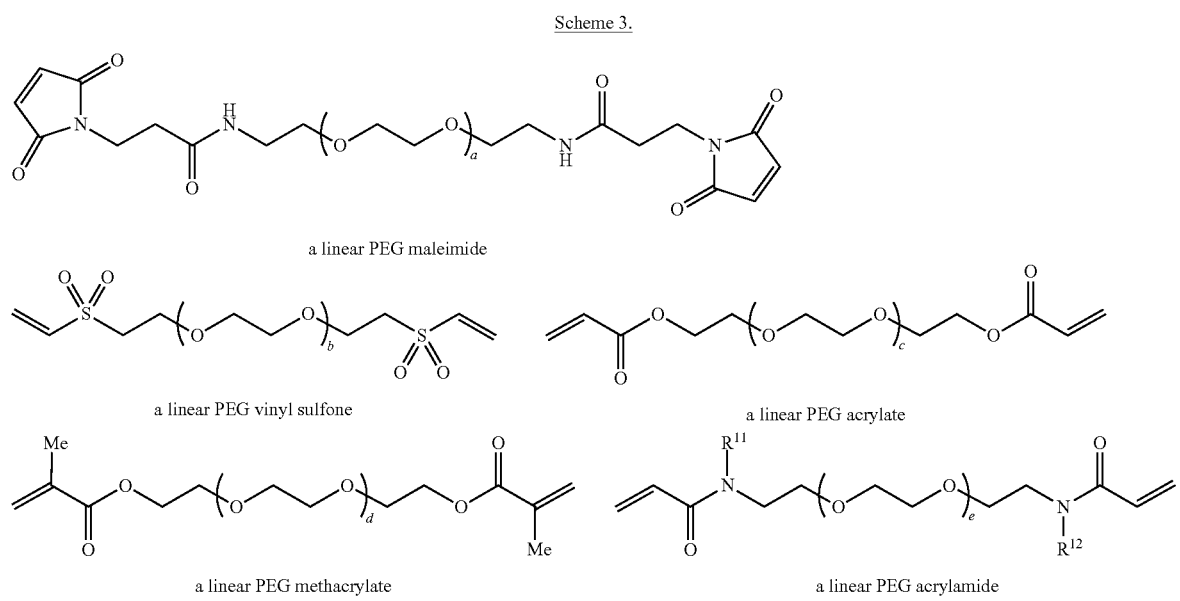

a linear PEG maleimide a linear PEG vinyl sulfone a linear PEG acrylate a linear PEG methacrylate a linear PEG acrylamide -continued

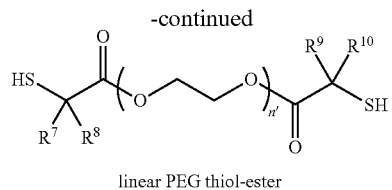

linear PEG thiol-ester

In any embodiment herein, the multi-arm PEG thiol-ester may be a 3-arm PEG thiol-ester, a 4-arm PEG thiol-ester, a 6-arm PEG thiol-ester, and 8-arm PEG thiol-ester, or a mixture of any two or more thereof.

Similar to the above, the PEG Michael acceptor may be a linear PEG Michael acceptor, a multi-arm PEG Michael acceptor, or a mixture thereof. The multi-arm PEG Michael acceptor may be a 3-arm PEG Michael acceptor, a 4-arm The amount of PEG Michael acceptor of any embodiment herein included in the second composition (by weight of the second composition) may be about 10 wt. %, about 12 wt. %, about 14 wt. %, about 16 wt. %, about 18 wt. %, about 20 wt. %, about 22 wt. %, about 24 wt. %, about 26 wt. %, about 28 wt. %, about 30 wt. %, about 32 wt. %, about 34 wt. %, about 36 wt. %, about 38 wt. %, about 40 wt. %, about 42 wt. %, about 44 wt. %, about 46 wt. %, about 48 wt. %, about 50 wt. %, or any range including and/or in between any two of these values.

In any embodiment herein, it may be that at least the PEG thiol, PEG thiol-ester, or mixture thereof includes a multi-arm PEG thiol, multi-arm PEG thiol-ester, or mixture thereof; it may be at least the PEG Michael acceptor includes a multi-arm PEG Michael acceptor. The amount of first composition and second composition in any embodiment herein may be the same in the hydrogel kit.

The PEG thiol of any embodiment herein may have a number average molecular weight ($M_n$) of about 100 g/mol to about 10,000 g/mol. The number average molecular weight of the PEG thiol of any embodiment herein may be 100 g/mol, 200 g/mol, 300 g/mol, 400 g/mol, 500 g/mol, 600 g/mol, 700 g/mol, 800 g/mol, 900 g/mol, 1,000 g/mol, 1,100 g/mol, 1,200 g/mol, 1,300 g/mol, 1,400 g/mol, 1,500 g/mol, 1,600 g/mol, 1,700 g/mol, 1,800 g/mol, 1,900 g/mol, 2,000 g/mol, 2,100 g/mol, 2,200 g/mol, 2,300 g/mol, 2,400 g/mol, 2,500 g/mol, 2,600 g/mol, 2,700 g/mol, 2,800 g/mol, 2,900 g/mol, 3,000 g/mol, 3,250 g/mol, 3,500 g/mol, 3,750 g/mol, 4,000 g/mol, 4,250 g/mol, 4,500 g/mol, 4,750 g/mol, 5,000 g/mol, 5,250 g/mol, 5,500 g/mol, 5,750 g/mol, 6,000 g/mol, 6,500 g/mol, 7,000 g/mol, 7,500 g/mol, 8,000 g/mol, 8,500 g/mol, 9,000 g/mol, 9,500 g/mol, or 10,000 g/mol.

The PEG thiol-ester of any embodiment herein may have a number average molecular weight ($M_n$) of about 100 g/mol to about 10,000 g/mol. Thus, in any embodiment herein, the number average molecular weight of the PEG thiol-ester of any embodiment herein may be 100 g/mol, 200 g/mol, 300 g/mol, 400 g/mol, 500 g/mol, 600 g/mol, 700 g/mol, 800 g/mol, 900 g/mol, 1,000 g/mol, 1,100 g/mol, 1,200 g/mol, 1,300 g/mol, 1,400 g/mol, 1,500 g/mol, 1,600 g/mol, 1,700 g/mol, 1,800 g/mol, 1,900 g/mol, 2,000 g/mol, 2,100 g/mol, 2,200 g/mol, 2,300 g/mol, 2,400 g/mol, 2,500 g/mol, 2,600 g/mol, 2,700 g/mol, 2,800 g/mol, 2,900 g/mol, 3,000 g/mol, 3,250 g/mol, 3,500 g/mol, 3,750 g/mol, 4,000 g/mol, 4,250 g/mol, 4,500 g/mol, 4,750 g/mol, 5,000 g/mol, 5,250 g/mol, 5,500 g/mol, 5,750 g/mol, 6,000 g/mol, 6,500 g/mol, 7,000 g/mol, 7,500 g/mol, 8,000 g/mol, 8,500 g/mol, 9,000 g/mol, 9,500 g/mol, or 10,000 g/mol.

The PEG Michael acceptor of any embodiment herein may have a number average molecular weight ($M_n$) of about 100 g/mol to about 10,000 g/mol. In any embodiment herein of the multi-arm PEG Michael acceptor, the number average molecular weight of the multi-arm PEG thiol-ester of any embodiment herein may be 100 g/mol, 200 g/mol, 300 g/mol, 400 g/mol, 500 g/mol, 600 g/mol, 700 g/mol, 800 g/mol, 900 g/mol, 1,000 g/mol, 1,100 g/mol, 1,200 g/mol, 1,300 g/mol, 1,400 g/mol, 1,500 g/mol, 1,600 g/mol, 1,700 g/mol, 1,800 g/mol, 1,900 g/mol, 2,000 g/mol, 2,100 g/mol, 2,200 g/mol, 2,300 g/mol, 2,400 g/mol, 2,500 g/mol, 2,600 g/mol, 2,700 g/mol, 2,800 g/mol, 2,900 g/mol, 3,000 g/mol, 3,250 g/mol, 3,500 g/mol, 3,750 g/mol, 4,000 g/mol, 4,250 g/mol, 4,500 g/mol, 4,750 g/mol, 5,000 g/mol, 5,250 g/mol, 5,500 g/mol, 5,750 g/mol, 6,000 g/mol, 6,500 g/mol, 7,000 g/mol, 7,500 g/mol, 8,000 g/mol, 8,500 g/mol, 9,000 g/mol, 9,500 g/mol, or 10,000 g/mol.

In any embodiment herein, the first pack composition and/or the second pack composition further include a therapeutic agent. The therapeutic agent may include an antibiotic, a corticosteroid, an aminoglycoside, a free radical scavenger agent, a small peptide therapeutic, a gene therapy related agent, or a combination of any two or more thereof. Exemplary antibiotics include ciprofloxacin and gacyclidine. Exemplary corticosteroids include, but are not limited to, dexamethasone, hydrocortisone, methylprednisolone, and prednisolone. Exemplary aminoglycosides include, but are not limited to, gentamicin, amikacin, streptomycin, neomycin, and tobramycin. Free radical scavengers include, but are not limited to, N-acetylcysteine (NAC), methionine, tocopherol, vitamin E, ebselen, tiopronin, organic thiophosphate, and copper compounds (such as inorganic copper (I) and or copper (II) salts). Small peptide therapeutics include, but are not limited to, an inhibitor for glycogen synthase kinase-3 beta (GSK3β), valproic acid, a TGF-β inhibitor, epidermal growth factor, basic fibroblast growth factor, insulin like growth factor 1, neurotrophin-3 (NT-3), an agonist for the GDNF receptor, and brain derived neurotrophic factor. Gene therapy related agents include, but are not limited to, a lipid vector, a viral vector, a non-viral vector, a nanoparticle, a cell-penetrating peptide (CPP and/or PTD), dendrimers, a polyplex, a liposome, a microsome, a polymersome, a lioplex, an oligonucleotide, naked DNA, small RNA, and CRISP-Cas9.

The amount of therapeutic agent in the first composition and/or second composition may be from 0.0001 wt. % to about 20 wt. % of the respective composition. Therefore, the amount of therapeutic agent may be about 0.0001 wt. %, about 0.0002 wt. %, about 0.0003 wt. %, about 0.0004 wt. %, about 0.0005 wt. %, about 0.0006 wt. %, about 0.0007 wt. %, about 0.0008 wt. %, about 0.0009 wt. %, about 0.001 wt. %, about 0.002 wt. %, about 0.003 wt. %, about 0.004 wt. %, about 0.005 wt. %, about 0.006 wt. %, about 0.007 wt. %, about 0.008 wt. %, about 0.009 wt. %, about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, about 2.2 wt. %, about 2.4 wt. %, about 2.6 wt. %, about 2.8 wt. %, about 3.0 wt. %, about 3.5 wt. %, about 4.0 wt. %, about 4.5 wt. %, about 5.0 wt. %, about 5.5 wt. %, about 6.0 wt. %, about 6.5 wt. %, about 7.0 wt. %, about 8.0 wt. %, about 9.0 wt. %, about 10.0 wt. %, about 11.0 wt. %, about 12.0 wt. %, about 13.0 wt. %, about 14.0 wt. %, about 15.0 wt. %, about 16.0 wt. %, about 17.0 wt. %, about 18.0 wt. %, about 19.0 wt. %, about 20.0 wt. %, or any range including and/or in between any two of these values.

In any embodiment herein, the first pack composition and/or the second pack composition further include a fluorescent moiety. The fluorescent moiety may be a fluorescent dye. Exemplary fluorescent dyes include, but are not limited to, N-(3-triethylammoniumpropyl)-4-(4-(dibutylamino) styryl) pyridinium dibromide, fluorescent gentamicin, phalloidin, Hoechst 33258 (CAS #: 23491-45-4), Hoechst 33342 (CAS #: 23491-52-3), Hoechst 34580 (CAS #: 23555-00-2), MitoTracker® Orange CMTMRos, MitoTracker® Red CMXRos, MitoTracker® Orange CM-H2TMRos, MitoTracker® Red CM-H2XRos, MitoTracker® Red FM, MitoTracker® Green FM, MitoTracker® Deep Red FM (MitroTracker® dyes available from, e.g., ThermoFisher Scientific), Qtracker® Cell Labeling Kits (available from, e.g., ThermoFisher Scientific), and carboxyfluorescein succinimidyl ester ("CFSE"), or a mixture of any two or more thereof. The amount of fluorescent moiety in the first composition and/or second composition may be from 0.0001 wt. % to about 20 wt. % of the respective composition. Therefore, the amount of fluorescent moiety may be about 0.0001 wt. %, about 0.0002 wt. %, about 0.0003 wt. %, about 0.0004 wt. %, about 0.0005 wt. %, about 0.0006 wt. %, about 0.0007 wt. %, about 0.0008 wt. %, about 0.0009 wt. %, about 0.001 wt. %, about 0.002 wt. %, about 0.003 wt. %, about 0.004 wt. %, about 0.005 wt. %, about 0.006 wt. %, about 0.007 wt. %, about 0.008 wt. %, about 0.009 wt. %, about 0.01 wt. %, about 0.02 wt. %, about 0.03 wt. %, about 0.04 wt. %, about 0.05 wt. %, about 0.06 wt. %, about 0.07 wt. %, about 0.08 wt. %, about 0.09 wt. %, about 1.0 wt. %, about 1.1 wt. %, about 1.2 wt. %, about 1.3 wt. %, about 1.4 wt. %, about 1.5 wt. %, about 1.6 wt. %, about 1.7 wt. %, about 1.8 wt. %, about 1.9 wt. %, about 2.0 wt. %, about 2.2 wt. %, about 2.4 wt. %, about 2.6 wt. %, about 2.8 wt. %, about 3.0 wt. %, about 3.5 wt. %, about 4.0 wt. %, about 4.5 wt. %, about 5.0 wt. %, about 5.5 wt. %, about 6.0 wt. %, about 6.5 wt. %, about 7.0 wt. %, about 8.0 wt. %, about 9.0 wt. %, about 10.0 wt. %, about 11.0 wt. %, about 12.0 wt. %, about 13.0 wt. %, about 14.0 wt. %, about 15.0 wt. %, about 16.0 wt. %, about 17.0 wt. %, about 18.0 wt. %, about 19.0 wt. %, about 20.0 wt. %, or any range including and/or in between any two of these values.

In any embodiment herein, the first pack composition and/or second pack composition may further include one or more buffer agents; and one or more tonicity agents. Exemplary tonicity agents and buffering agents are provided in *Remington's Pharmaceutical Sciences* (Alfonso Gennaro 18th ed. 1990) and Wade & Weller, HANDBOOK OF PHARMACEUTICAL EXCIPIENTS (1994), each of which is incorporated herein by reference. Thus, the one or more tonicity agents may include saccharose, glucose, glycerine, sorbitol, 1,2-propylene glycol, NaCl, KCl, $CaCl_2$, boric acid, citric acid, sodium tartrate, sodium phosphate, potassium phosphate, or mixtures of any two or more thereof. The one or more buffering agents may include citric acid, boric acid, phosphoric acid, trometamol, 3-[[1,3-dihydroxy-2-(hydroxymethyl)propan-2-yl]amino]propane-1-sulfonic acid ("TAPS"), 2-(Bis(2-hydroxyethyl)amino)acetic acid ("Bicine"), 2-Amino-2-(hydroxymethyl)propane-1,3-diol ("Tris"), N-(2-Hydroxy-1,1-bis(hydroxymethyl)ethyl)glycine ("Tricine"), 3-[[1,3-dihydroxy-2-(hydroxymethyl)propan-2-yl]amino]-2-hydroxypropane-1-sulfonic acid ("TAPSO"), 2-[[1,3-dihydroxy-2-(hydroxymethyl)propan-2-yl]amino]ethanesulfonic acid ("TES"), 3-Morpholinopropane-1-sulfonic acid ("MOPS"), 1,4-Piperazinediethanesulfonic acid ("PIPES"), 2-morpholin-4-ylethanesulfonic acid ("MES"), 2-[4-(2-hydroxyethyl)piperazin-1-yl]ethanesulfonic acid ("HEPES"), a pharmaceutically acceptable salt of any one or more thereof (e.g., sodium phosphate, potassium phosphate), or a combination of any two or more thereof. The first pack composition and/or second pack composition may exhibit a tonicity of about 290 mOsm to about 320 mOsm.

Further, the first pack composition and/or second pack composition may exhibit a dynamic viscosity of about 0.001 to about 1 Pa·s. Thus, the dynamic viscosity of any embodiment of the first pack composition and/or any embodiment of the second pack composition may be about 0.001 Pa·s, about 0.002 Pa·s, about 0.003 Pa·s, about 0.004 Pa·s, about 0.005 Pa·s, about 0.006 Pa·s, about 0.007 Pa·s, about 0.008 Pa·s, about 0.009 Pa·s, about 0.01 Pa·s, about 0.02 Pa·s, about 0.03 Pa·s, about 0.04 Pa·s, about 0.05 Pa·s, about 0.06 Pa·s, about 0.07 Pa·s, about 0.08 Pa·s, about 0.09 Pa·s, about 1.0 Pa·s, or any range including and/or in between any two of these values.

Upon combining the first pack composition and the second pack composition, a hydrogel is produced. Thus, the hydrogel kit may further include instructions for combining the first pack composition and the second pack composition to produce the hydrogel. This hydrogel includes a cross-linked polymer formed by cross-linking of the multi-arm PEG thiol, the multi-arm PEG thiol-ester, or a mixture thereof with the multi-arm PEG Michael acceptor. The hydrogel may include the therapeutic agent of any embodiment herein from 0.001 wt. % to about 20 wt. % by weight of the hydrogel (or any of the previously recited ranges and/or values). The hydrogel may exhibit a tonicity of about 290 mOsm to about 320 mOsm. The hydrogel may exhibit a dynamic viscosity of about 2 to about 1000 Pa·s. Thus, the dynamic viscosity of any embodiment of the hydrogel may be about 2 Pa·s, about 3 Pa·s, about 4 Pa·s, about 5 Pa·s, about 6 Pa·s, about 7 Pa·s, about 8 Pa·s, about 9 Pa·s, about 10 Pa·s, about 15 Pa·s, about 20 Pa·s, about 30 Pa·s, about 40 Pa·s, about 50 Pa·s, about 60 Pa·s, about 70 Pa·s, about 80 Pa·s, about 90 Pa·s, about 100 Pa·s, about 200 Pa·s, about 300 Pa·s, about 400 Pa·s, about 500 Pa·s, about 600 Pa·s, about 700 Pa·s, about 800 Pa·s, about 900 Pa·s, about 1000 Pa·s, or any range including and/or in between any two of these values.

The hydrogel kit of any embodiment herein may be a medical kit, where such a medical kit further includes one or more of a cannula (such as tubing), an apparatus for combining the first and second composition (such as when the first and second composition are flowed through independent cannula and combined via the apparatus, and dispensed either from the apparatus or from an additional cannula exiting the apparatus), or a needle. The needle may be configured to infuse the first pack composition through a cannula; the needle may be configured to infuse the first pack composition through a cannula; the needle may be configured to deliver a combination of the first and second composition (provided by, e.g., the apparatus) to a site. In any embodiment herein of the medical kit, the cannula may be microfluidic tubing. In any embodiment herein of the medical kit. The medical kit may further include instructions for use of any one or more of the cannula, apparatus, and needle administering the hydrogel to a subject.

Drug Delivery and Treatment Methods of the Present Technology

The present disclosure provides methods for delivering drugs directly into the cochlear fluids in a minimally invasive manner. In some embodiments, the method comprises administering to the subject an effective amount of the gel precursor solutions disclosed herein (which include an inner ear-specific therapeutic agent), wherein the gel precursor solutions are administered through a cannula that accesses a cochleostomy site (e.g., the scala tympani) or a canalostomy site in the inner ear of the subject, and the cannula is surgically sealed/removed after the gel-based precursor solutions are delivered. The gel precursor solutions form a hydrogel in situ that is biodegradable, produces non-ototoxic products upon degradation, and has an elastic modulus between 1 and 1,000 kPa. The therapeutic agent released from the gel matrix diffuses and spreads through the perilymphatic fluid over time, eventually interacting with hearing-related targets such as hair cells or neural cells within the inner ear spaces. FIGS. 1(a)-1(b) show the chemical design and projected delivery/degradation kinetics of a biodegradable gel designed to be administered directly into the cochlear fluids of a subject that suffers from hearing loss or auditory disease.

While gel-based delivery from intracochlear placement is impacted by variation in the drug release rate from the gel matrix, one advantage of the methods disclosed herein is that the released drug does not have to diffuse through intervening tissues and structures between the delivery site and the target site. Given its biodegradable properties, the gel matrix does not affect or damage hearing once the delivery process is completed.

In one aspect, the present disclosure provides a method for treating an auditory disease or hearing loss in a subject in need thereof comprising administering an effective amount of a first pack composition and an effective amount of a second pack composition to the subject, wherein (a) the first pack composition comprises about 10 wt. % to about 50 wt. % by weight of the first pack composition of a PEG thiol, a PEG thiol-ester, or a mixture thereof; and water; (b) the second pack composition comprises about 10 wt. % to about 50 wt. % by weight of the second pack composition of a PEG Michael acceptor; and water; and (c) the first pack composition and/or the second pack composition further comprises at least one inner ear-specific therapeutic agent, wherein the first pack composition and/or the second pack composition is administered through a cannula that penetrates the round window membrane of the subject.

In another aspect, the present disclosure provides a method for treating an auditory disease or hearing loss in a subject in need thereof comprising administering an effective amount of a first pack composition and an effective amount of a second pack composition to the subject, wherein (a) the first pack composition comprises about 10 wt. % to about 50 wt. % by weight of the first pack composition of PEG thiol, a PEG thiol-ester, or a mixture thereof; and water; (b) the second pack composition comprises about 10 wt. % to about 50 wt. % by weight of the second pack composition of a PEG Michael acceptor; and water; and (c) the first pack composition and/or the second pack composition further comprises at least one inner ear-specific therapeutic agent, wherein the first pack composition and/or the second pack composition is administered through a cannula that accesses a cochleostomy site or a canalostomy site in the inner ear of the subject. In some embodiments, the cochleostomy site is located within the cochlear bone of the subject. In certain embodiments, the canalostomy site is located within the semicircular canals of the subject. Additionally or alternatively, in some embodiments, the method further comprises resealing the cannula with sodium hyaluronate, a muscle graft, a fat graft, or a fascia graft.

In any of the above embodiments of the methods disclosed herein, a microfluidic tubing or a high-gauge needle is used to infuse the first pack composition and/or the second pack composition through the cannula. In certain embodiments, the first pack composition and/or the second pack composition is administered into a fluid-filled cochlear tube selected from the group consisting of scala tympani (ST), scala vestibuli, and scala media. In any of the above embodiments of the methods disclosed herein, the first pack composition and/or the second pack composition form a hydrogel in situ having an elastic modulus between 1 and 1,000 kPa.

Additionally or alternatively, in some embodiments of the methods disclosed herein, the at least one inner ear-specific therapeutic agent comprises a corticosteroid, an aminoglycoside, a free radical scavenger agent, a small peptide therapeutic, a gene therapy related agent, or a combination of any two or more thereof. The at least one inner ear-specific therapeutic agent may comprise ciprofloxacin, gacyclidine, a γ-secretase inhibitor, dexamethasone, hydrocortisone, methylprednisolone, prednisolone, gentamicin, amikacin, streptomycin, neomycin, tobramycin, N-acetylcysteine (NAC), methionine, tocopherol, vitamin E, ebselen, tiopronin, organic thiophosphate, copper compounds, an inhibitor for glycogen synthase kinase-3 beta (GSK3β), valproic acid, a TGF-β inhibitor, epidermal growth factor, basic fibroblast growth factor, insulin like growth factor 1, neurotrophin-3 (NT-3), an agonist for the GDNF receptor (e.g., XIB4035), brain derived neurotrophic factor, a lipid vector, a viral vector, a non-viral vector, a polyplex, a liposome, a microsome, a polymersome, a lioplex, an oligonucleotide, naked DNA, small RNA, CRISP-Cas9, or a combination of any two or more thereof.

Additionally or alternatively, in some embodiments of the methods disclosed herein, the first pack composition and the second pack composition are administered simultaneously or sequentially. The first pack composition and/or the second pack composition may be administered as a single injection or multiple injections. In some embodiments of methods of the present technology, the subject is human.

Additionally or alternatively, in some embodiments of the methods disclosed herein, the first pack composition and/or the second pack composition further comprises a fluorescent tracer compound. The fluorescent tracer compound may be selected from the group consisting of FM 1-43 FX, GTTR, Phalloidin, Hoechst, Mitotracker, Q-tracker, and CFSE.

In any of the above embodiments of the methods disclosed herein, the auditory disease is selected from the group consisting of sensorineural hearing loss, noise-induced hearing loss, sudden sensorineural hearing loss, autoimmune inner ear disease, tinnitus, cisplatin ototoxicity protection, radiation-induced ototoxicity protection, Meniere's disease, and cranial nerve schwannoma. In certain embodiments of the methods, the administration of the first pack composition and/or the second pack composition results in an increase in survival and/or regeneration of inner hair cells or outer hair cells. Additionally or alternatively, in some embodiments of the methods disclosed herein, the administration of the first pack composition and/or the second pack composition results in an improvement of one or more electrophysiological parameters selected from the group consisting of Auditory Brainstem Response, Compound Action Potential, hearing thresholds, and Distortion Product Optoacoustic Emissions relative to that observed in an untreated control subject having auditory disease.

In one aspect, the present disclosure provides a method for treating an auditory disease or hearing loss in a subject in need thereof comprising (a) attaching a pump containing at least one inner ear-specific therapeutic agent to the cochlea of the subject, and (b) administering to the subject an effective amount of the at least one inner ear-specific therapeutic agent, wherein the pump infuses the at least one inner ear-specific therapeutic agent through a cannula that penetrates the round window membrane of the subject. In another aspect, the present disclosure provides a method for treating an auditory disease or hearing loss in a subject in need thereof comprising (a) attaching a pump containing at least one inner ear-specific therapeutic agent to the cochlea of the subject, and (b) administering to the subject an effective amount of the at least one inner ear-specific therapeutic agent, wherein the pump infuses the at least one inner ear-specific therapeutic agent through a cannula that accesses a cochleostomy site or a canalostomy site in the inner ear of the subject. In some embodiments, the cochleostomy site is located within the cochlear bone of the subject. In certain embodiments, the canalostomy site is located within the semicircular canals of the subject. Additionally or alternatively, in some embodiments, the method further comprises resealing the cannula with sodium hyaluronate, a muscle graft, a fat graft, or a fascia graft.

Additionally or alternatively, in some embodiments of the methods disclosed herein, the pump may be a micropump that is head-worn or implanted (if drug delivery is to be maintained for a period of days, weeks or months), so that the subject may remain ambulatory during the drug delivery process. The pump may be used for short-term single infusions into the cochlea, multiple infusions into the cochlea, or extended, continuous or chronic use.

In any of the above embodiments, the at least one inner ear-specific therapeutic agent may in the form of a lyophilized powder, a fluid bolus, or contained within a gel or particle matrix. The therapeutic agents described herein may be formulated at any suitable concentration to achieve the daily doses according to the selected delivery regimen.

By way of example, a therapeutic agent may be formulated at concentrations of between about 10 mg/ml and about 500 mg/ml.

The therapeutic agents may be formulated as solutions, suspensions, dispersions, and any class of nanocolloidal carrier including polymeric nanoparticles, liposome, polymeric micelles and suspension of solid lipid nanoparticles having a median particle size of less than 1 micron.

Dispersions may be formulated according to techniques well known in the art (see, for example, Remington's Pharmaceutical Sciences, Chapter 43, 14th Ed., Mack Publishing Co., Easton, Pa.), using suitable dispersing or wetting and suspending agents, such as sterile oils, including synthetic mono- or diglycerides, and fatty acids, including oleic acid. Fluid compositions containing large molecules may be prepared in water, saline, isotonic saline, phosphate-buffered saline, citrate-buffered saline, and the like and may optionally be mixed with a nontoxic surfactant. Dispersions may also be prepared in glycerol, liquid polyethylene, glycols, DNA, vegetable oils, triacetin, and the like and mixtures thereof. These preparations may contain a preservative to prevent the growth of microorganisms. Pharmaceutical dosage forms suitable for injection or infusion include sterile, aqueous solutions, suspensions, or dispersions or sterile powders comprising an active ingredient which powders are adapted for the extemporaneous preparation of sterile injectable or infusible solutions or dispersions. The ultimate dosage form is a sterile fluid and stable under the conditions of manufacture and storage. A liquid carrier or vehicle of the solution, suspension or dispersion may be a diluent or solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. Proper fluidity of solutions, suspensions or dispersions may be maintained, for example, by the formation of liposomes, by the maintenance of the desired particle size, in the case of dispersion, or by the use of nontoxic surfactants.

Antibacterial and antifungal agents, for example, parabens, chlorobutanol, phenol, sorbic acid, thimerosal, ethanol and the like may be included. In many cases, isotonic agents, for example, sugars, buffers, or sodium chloride may be included. Prolonged absorption of the compositions can be brought about by the inclusion in the composition of agents delaying absorption, for example, aluminum monosterate hydrogels and gelatin. Excipients that increase solubility, such as cyclodextrin, may be added. The concentration of large molecules may be readily determined and varied as conditions warrant based on the disease to be treated or the response of the subject to the treatment. For prolonged delivery of a fluid composition to a subject, it may be desirable for the composition to be isotonic tissue into which the composition is being delivered. For example, the fluid composition may be isotonic with a subject's perilymphatic fluid.

Fluid compositions intended for intracochlear delivery may have a tonicity of about 290 mOsm to about 320 mOsm. If during formulation the composition has a tonicity lower than about 290 mOsm to about 320 mOsm, the tonicity may be enhanced by adding a tonicity enhancing agent, such as sodium chloride. As used herein, "tonicity enhancing agent" means a compound or composition that increases tonicity of a composition. In some embodiments, an additional therapeutic agent, stabilizing compound, preservative, solubilizing agent, buffer, etc., may be added. Sterile fluid compositions may be prepared by incorporating the large molecule in the desired amount in the appropriate diluent or solvent with various other ingredients, e.g. as enumerated above, and, as desired, followed by sterilization. Any means for sterilization may be used. For example, sterilization may be accomplished by heating, filtering, aseptic technique, and the like, or a combination thereof. In some circumstances it may be desirable to obtain a sterile powder for the preparation of sterile solutions.

If the delivery process is acute or short-term, the pump may be a large device that is deployed while the subject is sedated. In either case, following the appropriate delivery sequence, the pump is removed and the surgical access site is closed/sealed. For pump-based delivery, once the pump is removed, the continued diffusion and spreading of the at least one inner ear-specific therapeutic agent is dependent on the starting drug concentration, the diffusion coefficient/molecular weight of the therapeutic agent, electrical effects such as molecular charge, drug binding to proteins, and other effects that are described herein.

Examples of inner ear-specific therapeutic agents include corticosteroids, aminoglycosides, free radical scavenger agents, small peptide therapeutics, gene therapy related agents, or a combination of any two or more thereof. The at least one inner ear-specific therapeutic agent may comprise ciprofloxacin, gacyclidine, a γ-secretase inhibitor, dexamethasone, hydrocortisone, methylprednisolone, prednisolone, gentamicin, amikacin, streptomycin, neomycin, tobramycin, N-acetylcysteine (NAC), methionine, tocopherol, vitamin E, ebselen, tiopronin, organic thiophosphate, copper compounds, an inhibitor for glycogen synthase kinase-3 beta (GSK3β), valproic acid, a TGF-β inhibitor, epidermal growth factor, basic fibroblast growth factor, insulin like growth factor 1, neurotrophin-3 (NT-3), an agonist for the GDNF receptor (e.g., XIB34035), brain derived neurotrophic factor, a lipid vector, a viral vector, a non-viral vector, a polyplex, a liposome, a microsome, a polymersome, a lioplex, an oligonucleotide, naked DNA, small RNA, CRISP-Cas9, or a combination of any two or more thereof.

In any of the above embodiments of the methods disclosed herein, the auditory disease is selected from the group consisting of sensorineural hearing loss, noise-induced hearing loss, sudden sensorineural hearing loss, autoimmune inner ear disease, tinnitus, cisplatin ototoxicity protection, radiation-induced ototoxicity protection, Meniere's disease, and cranial nerve schwannoma. In certain embodiments of the methods, the administration of the at least one inner ear-specific therapeutic agent results in an increase in survival and/or regeneration of inner hair cells or outer hair cells. Additionally or alternatively, in some embodiments of the methods disclosed herein, the administration of the at least one inner ear-specific therapeutic agent results in an improvement of one or more electrophysiological parameters selected from the group consisting of Auditory Brainstem Response, Compound Action Potential, hearing thresholds, and Distortion Product Optoacoustic Emissions relative to that observed in an untreated control subject having auditory disease.

Also disclosed herein are methods for evaluating the concentration of therapeutic agents within the cochlea of a subject comprising attaching a micropump-based sampling device to the cochlea of the subject, wherein the micropump-based sampling device is attached to a cannula that penetrates the round window membrane of the subject. The present disclosure also provides methods for evaluating the concentration of therapeutic agents within the cochlea comprising attaching a micropump-based sampling device to the cochlea of the subject, wherein the micropump-based sampling device is attached to a cannula that accesses a cochleostomy site or a canalostomy site in the inner ear of the subject. In some embodiments, the cochleostomy site is located within the cochlear bone of the subject. In certain embodiments, the canalostomy site is located within the semicircular canals of the subject. Additionally or alternatively, in some embodiments, the method further comprises resealing the cannula with sodium hyaluronate, a muscle graft, a fat graft, or a fascia graft.

The present disclosure also provides methods that are useful for evaluating the efficacy and/or safety of the various delivery approaches that are used to achieve therapeutic effects with drugs dispensed directly into inner ear fluids. These methods include computational modeling, hearing measurements, and histopathology assessment steps, to be used in conjunction with the drug delivery methods described herein.

Computational modeling is used to simulate drug delivery/transport based on direct intracochlear access while accounting for mechanisms that regulate drug concentration such as axial diffusion, radial diffusion, convective effects from the pump, clearance down the cochlear aqueduct, variation in diameter of the Scala Tympani, drug binding to proteins present in the cochlear fluids, and cyclic or repeated elements of the delivery protocol.

Hearing measurements assay the effects of therapeutic compounds in the inner ear. Use of hearing measurements in combination with temporary, direct intracochlear delivery and transport cycles, computational modeling, and histopathology are useful for evaluating the efficacy and safety of a therapeutic agent.

Histopathology using whole mount or sectioning of the cochleae following delivery cycles, may be used as a semi-quantitative means to assess drug delivery/transport from a temporarily implanted gel or pump within cochlear structures. Examples of histopathologic assessment using fluorescent tracer compounds such as FM-143 and QTracker, and visualizing the same using confocal microscopy, are shown in FIG. 5, along with the estimated concentration gradient and pharmacokinetics profile.

In one aspect, the present disclosure provides methods for assessing the efficacy of a therapeutic agent in the treatment of an inner ear disease comprising (1) administering an effective amount of any first pack composition described herein and an effective amount of any second pack composition described herein to the subject, wherein the first pack composition and/or the second pack composition further comprises the therapeutic agent, wherein the first pack composition and/or the second pack composition is administered through a cannula that penetrates the round window membrane of the subject or through a cannula that accesses a cochleostomy site or a canalostomy site in the inner ear of the subject; (2) evaluating the hearing response and/or histology of cochlear cells, tissues and/or hearing structures of the subject following administration of the first pack composition and the second pack composition; and (3) determining that the therapeutic agent is effective in treating the inner ear disease when the subject exhibits amelioration of hearing loss and/or increased survival or regeneration of inner hair cells or outer hair cells compared to an untreated subject with hearing loss.

In another aspect, the present disclosure provides methods for assessing the efficacy of a therapeutic agent in the treatment of an inner ear disease comprising (1) attaching a pump containing the therapeutic agent to the cochlea of the subject; (2) administering to the subject an effective amount of the therapeutic agent, wherein the pump infuses the therapeutic agent through a cannula that penetrates the round window membrane of the subject or through a cannula that accesses a cochleostomy site or a canalostomy site in the inner ear of the subject; (3) evaluating the hearing response and/or histology of cochlear cells, tissues and/or hearing structures of the subject following administration of the therapeutic agent; and (4) determining that the therapeutic agent is effective in treating the inner ear disease when the subject exhibits amelioration of hearing loss and/or increased survival or regeneration of inner hair cells or outer hair cells compared to an untreated subject with hearing loss.

In some embodiments of the methods disclosed herein, the cochleostomy site is located within the cochlear bone of the subject. In certain embodiments of the methods disclosed herein, the canalostomy site is located within the semicircular canals of the subject. Additionally or alternatively, in some embodiments, the methods further comprise resealing the cannula with sodium hyaluronate, a muscle graft, a fat graft, or a fascia graft.

In addition to monitoring hearing thresholds, amplitudes of CAP, ABR, or DPOAE may be monitored to generate pharmacokinetic drug profiles during for either short-term (acute) or long-term (chronic) evaluation. The histology of cochlear cells, tissues and/or hearing structures may be assessed using a fluorescent tracer compound as described herein.

EXAMPLES

Example 1

Figure 1D:
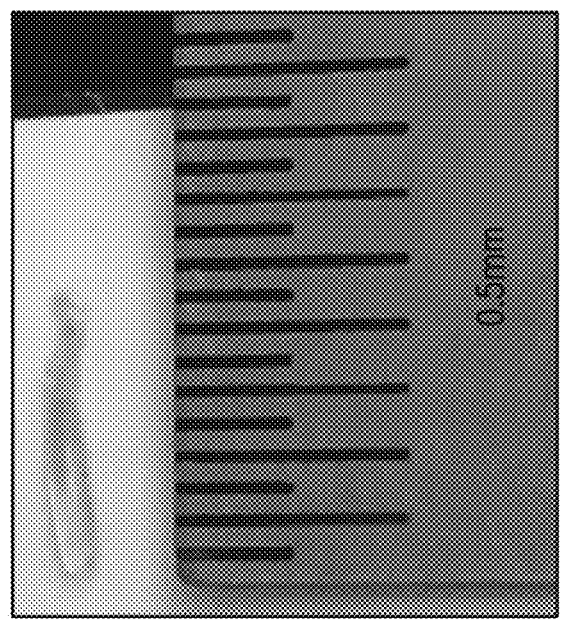
Figure 1C:
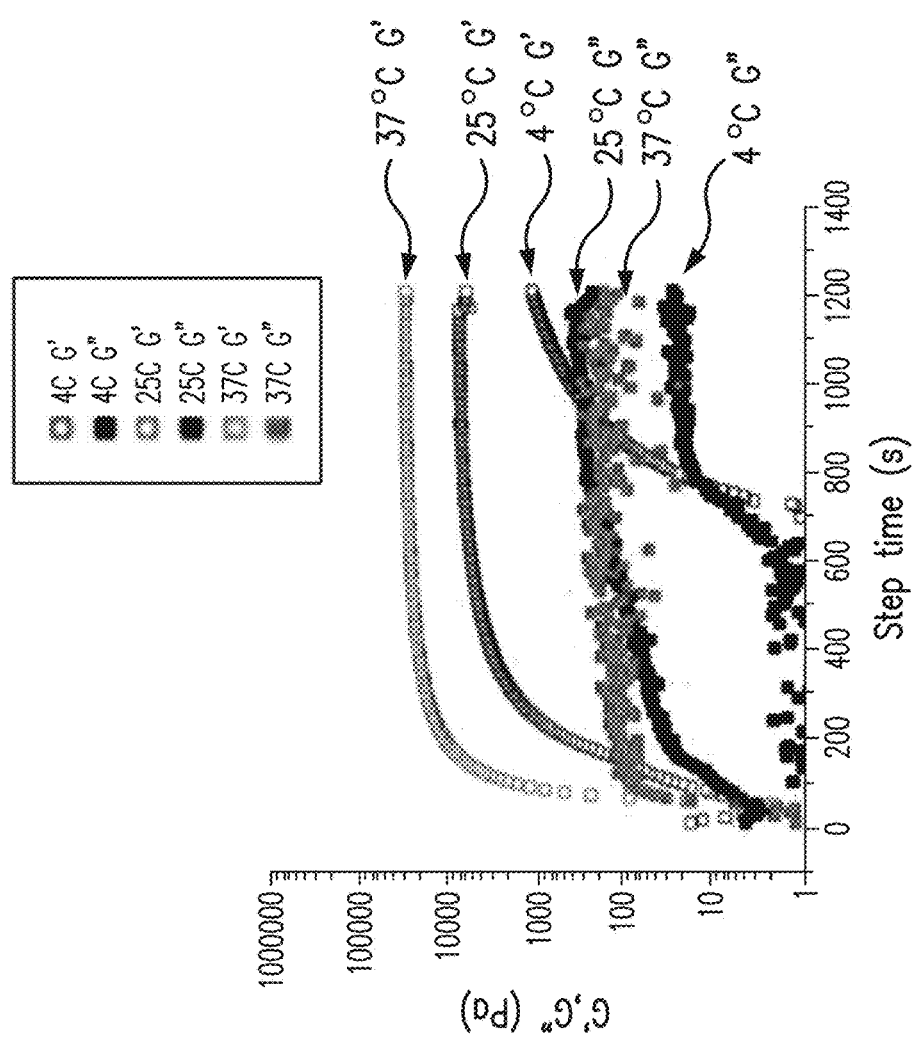
Figure 2A:
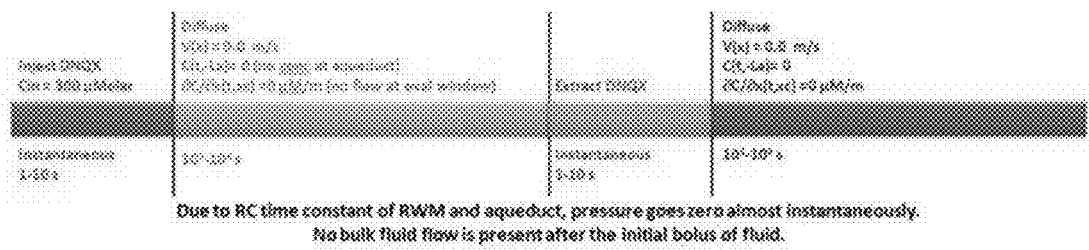
FIG. 2(a), FIG. 2(b), FIG. 2(c), FIG. 2(d), and FIG. 2(e) show the computational modeling results of the drug delivery experiments described herein, where various equations characterize the factors controlling drug concentration such as diffusion, convection, drug binding, drug clearance, changes to the radius of the scala tympani, etc.
Figure 2B:
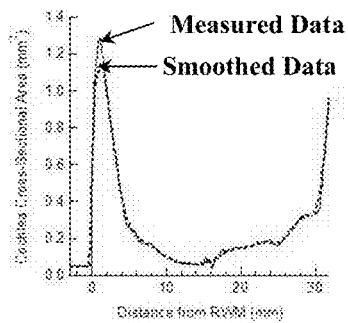
Figure 2C:
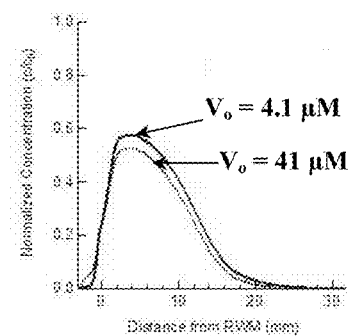
Figure 2D:
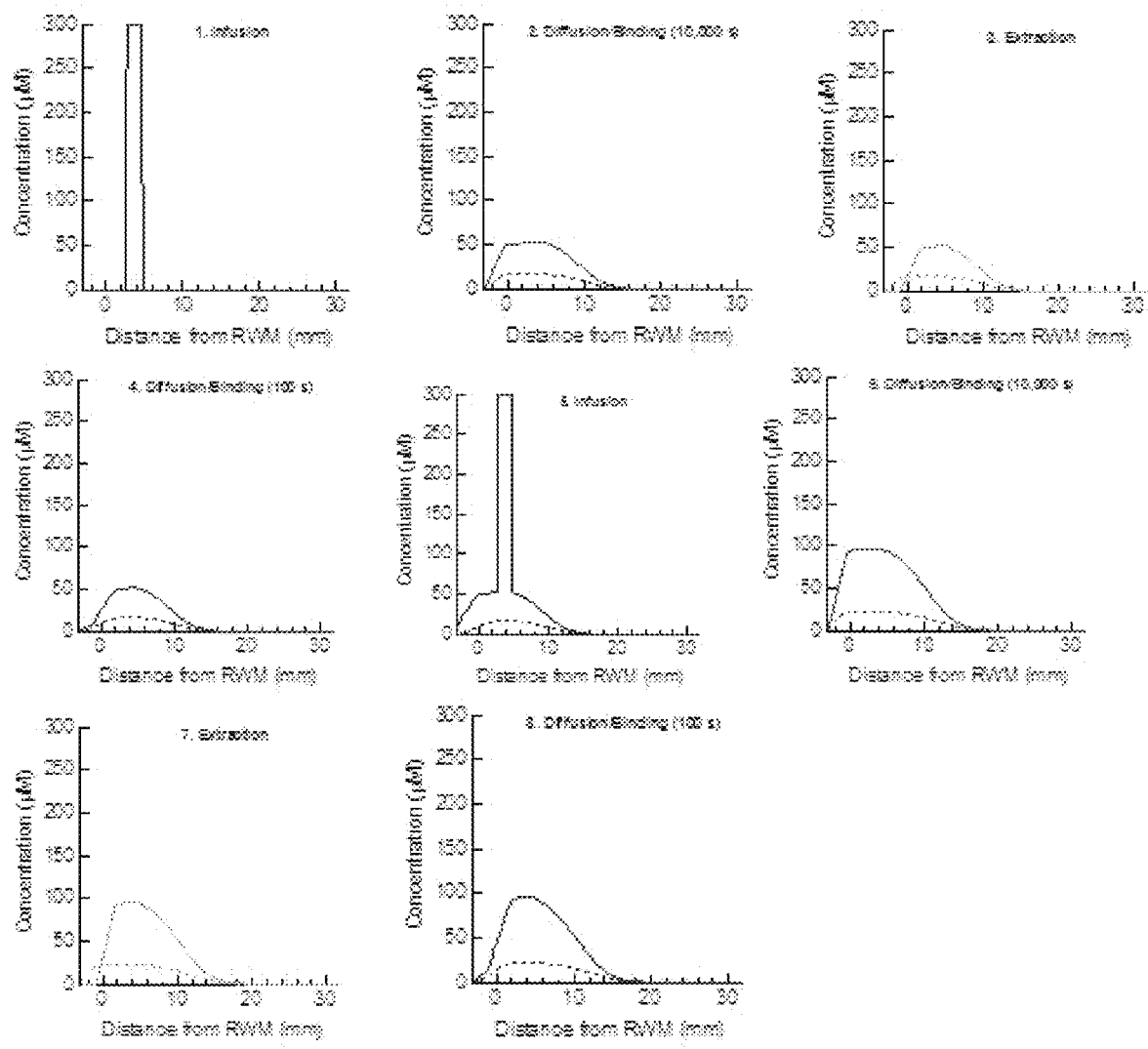
Figure 2E:
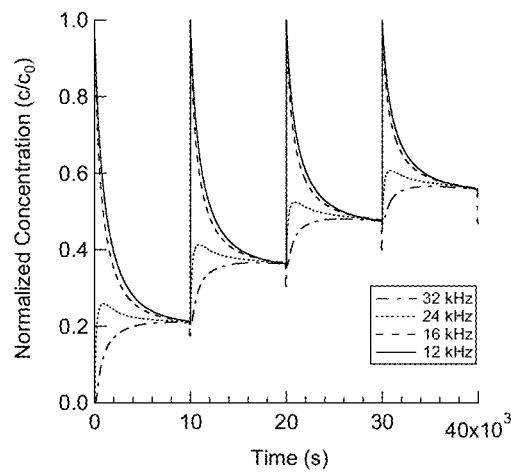
Figure 2E:
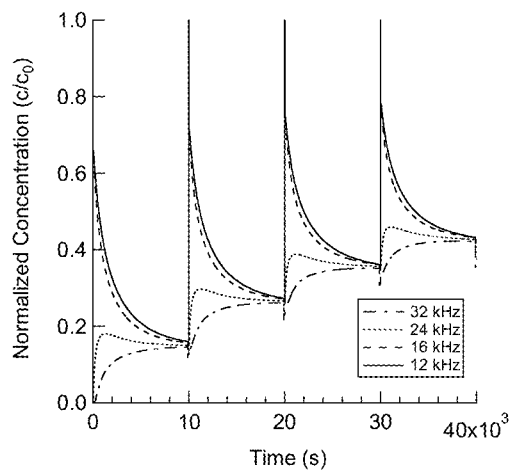
Figure 2E:
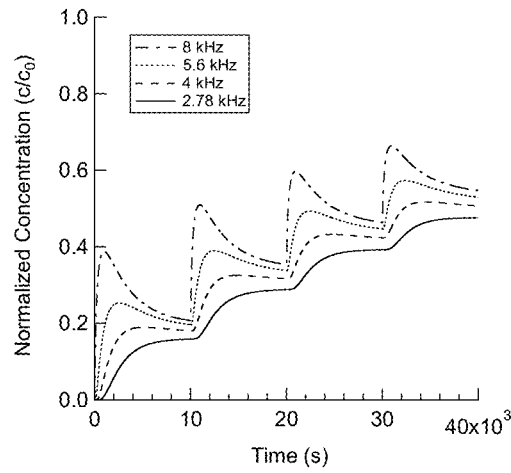
Figure 2E:
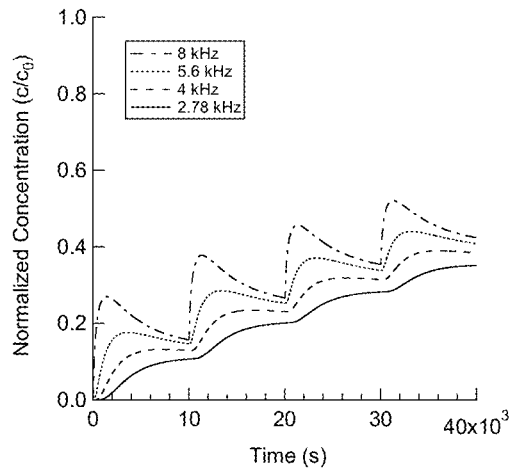

Materials and Methods for Preparing the Gel Compositions of the Present Technology Testing of hydrogel formation kinetics. Gels were formed by step growth polymerization of 3-arm thiol-esters and PEG-diacrylate by the thiol-type Michael Addition mechanism. Stoichiometric quantities of 3-arm thiol-esters and PEG-diacrylate were dissolved separately at 25 wt. % in buffered artificial perilymph solution (mM: NaCl, 120; KCl, 3.5; CaCl$_2$, 1.5; glucose, 5.5; HEPES, 20). These prepolymer solutions were cooled to 4° C. to improve solubility and then combined and mixed by vortex. Rheology was performed on a Discovery Hybrid rheometer from TA instruments (Newcastle, Del.). After mixing, 250 μL of the prepolymer solution was injected onto a Peltier plate with temperature control. A 20 mm circular overhead plate was used to apply 0.5% strain at 10 rad/sec and collect data for 10 minutes as gelation occurred. FIG. 1(c) shows the dynamic rheology plots showing evolution of hydrogel network formation: G' (storage modulus) and G" (loss modulus) at 4° C., 25° C., and 37° C.

In vitro swelling and degradation studies. Swelling and degradation studies were performed by measuring wet mass of the hydrogel at various time points. The swelling ratio Q was calculated as:

$$Q = \frac{m_x - m_o}{m_o}$$

where $m_x$ is the wet mass of the hydrogel sample at a time x, and $m_o$ is the wet mass of the hydrogel sample immediately after gelation.

Simulation of intracochlear hydrogel injection. Hydrogel formation in the cochlea was simulated in vitro by injection of prepolymer components through a microfluidic device into capillary tubes containing artificial perilymph. The microfluidic device was constructed from commercially available components; 150 μm ID PEEK tubing was purchased from Idex (Oak Harbor, Wash.), Y-interconnectors and two-piece microfluidic adapters were purchased from LabSmith (Livermore, Calif.), and 250 μL 1700 Series syringes with Luer Lock adapters were purchased from Hamilton (Reno, Nev.). Two syringes were loaded with the prepolymer components (either 3-arm thiol-ester or PEG-diacrylate) and placed in parallel on a Harvard PHD ULTRA™ syringe pump (Harvard Apparatus—Holliston, Mass.). The prepolymer components are combined trough the Y-connector, which merges inlet tubing from each of the syringes. A 10 cm length of PEEK tubing exits the outlet port of the Y-connector and terminates in a 5 mm length of 100 μm ID Teflon tubing, procured from Grainger (Everett, Mass.), that serves as a cannula for intracochlear injection. In the simulation experiment, the cannula was inserted 3 mm into a 0.5 mm ID glass capillary tube containing artificial perilymph heated to 37° C. Two μL of the prepolymer solution was injected at a rate of 1 μL/min. Approximately 10 minutes after the injection, the capillary tube was opened to examine the hydrogel. FIG. 1(d) shows a hydrogel formed after injection into a capillary tube at 4° C.

In vitro FITC-dextran release studies. Release profiles of macromolecular solutes from the hydrogels were studied using fluorescent dextran (FITC-dextran) drug surrogates of various molecular weights (3 kDa, 10 kDa, 20 kDa, 40 kDa). FITC-dextran was loaded in hydrogel precursor solution at 2 mg/mL, prior to gelation. Hydrogel discs (d=5 mm, h=3 mm) were formed in silicone molds, and incubated at 37° C. in 1 mL of PBS (1×) with gentle stirring. Aliquots of receptor solution were collected with replacement and analyzed for fluorescent intensity.

Example 2

Evaluation of Efficacy of the Drug Delivery Methods of the Present Technology

This Example demonstrates that the methods of the present technology are useful for delivering drugs into the cochlea via the perilymphatic fluid and for monitoring the histological effects on cochlear cells, tissues and hearing structures in a subject.

Computational modeling was used to simulate drug delivery/transport based on direct intracochlear administration, while accounting for the principal mechanisms controlling drug concentration during these processes such as axial diffusion, radial diffusion, convective effects from a pump, clearance down the cochlear aqueduct, variation in diameter of the Scala Tympani, drug binding to proteins present in the cochlear fluids, and cyclic or repeated elements of the delivery protocol. FIGS. 2(a)-(e) show an exemplary computational model, where the salient boundary conditions and plots of concentration versus distance and location within the cochlea are provided.

Reciprocating inner ear delivery and electronically-controlled dosing in a guinea pig model using a pump to infuse a drug via a cochleostomy (made at the basal turn) was evaluated. The drug reservoir was loaded with the glutamate receptor antagonist DNQX (which disrupts hair-cell-to-auditory-nerve synaptic transmission resulting in attenuation of compound action potentials (CAPs) generated in response to auditory stimuli). The molecular weight (232 Daltons) and physicochemical characteristics of DNQX make it a suitable model for evaluating the potential of other small molecule candidates for inner ear delivery. Further, the dose-dependent ability of DNQX to block the tone-pip-evoked compound action potential (CAP) permits monitoring of the drug distribution along the length of the cochlea with the drug's electrophysiological effects serving as a surrogate for drug concentration. DPOAE responses from hair cells (which are not altered by DNQX) were monitored as a control for nonspecific effects.

Figure 3A:
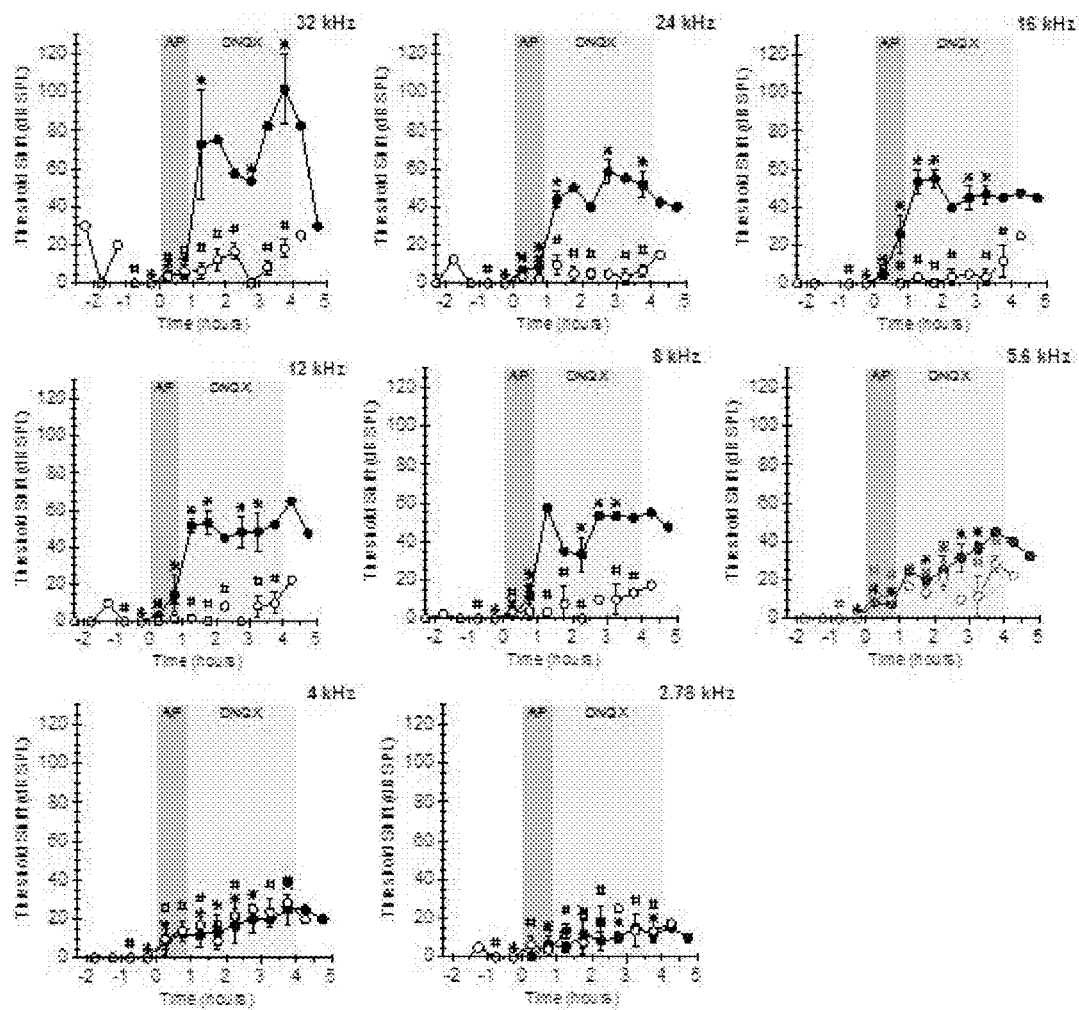
FIG. 3(a), and FIG. 3(b) show the hearing measurements for drug delivery experiments where the drug simulant DNQX (which is capable of temporarily blocking afferent synaptic transmission of auditory signals) is delivered acutely using a micropump.
Figure 3B:
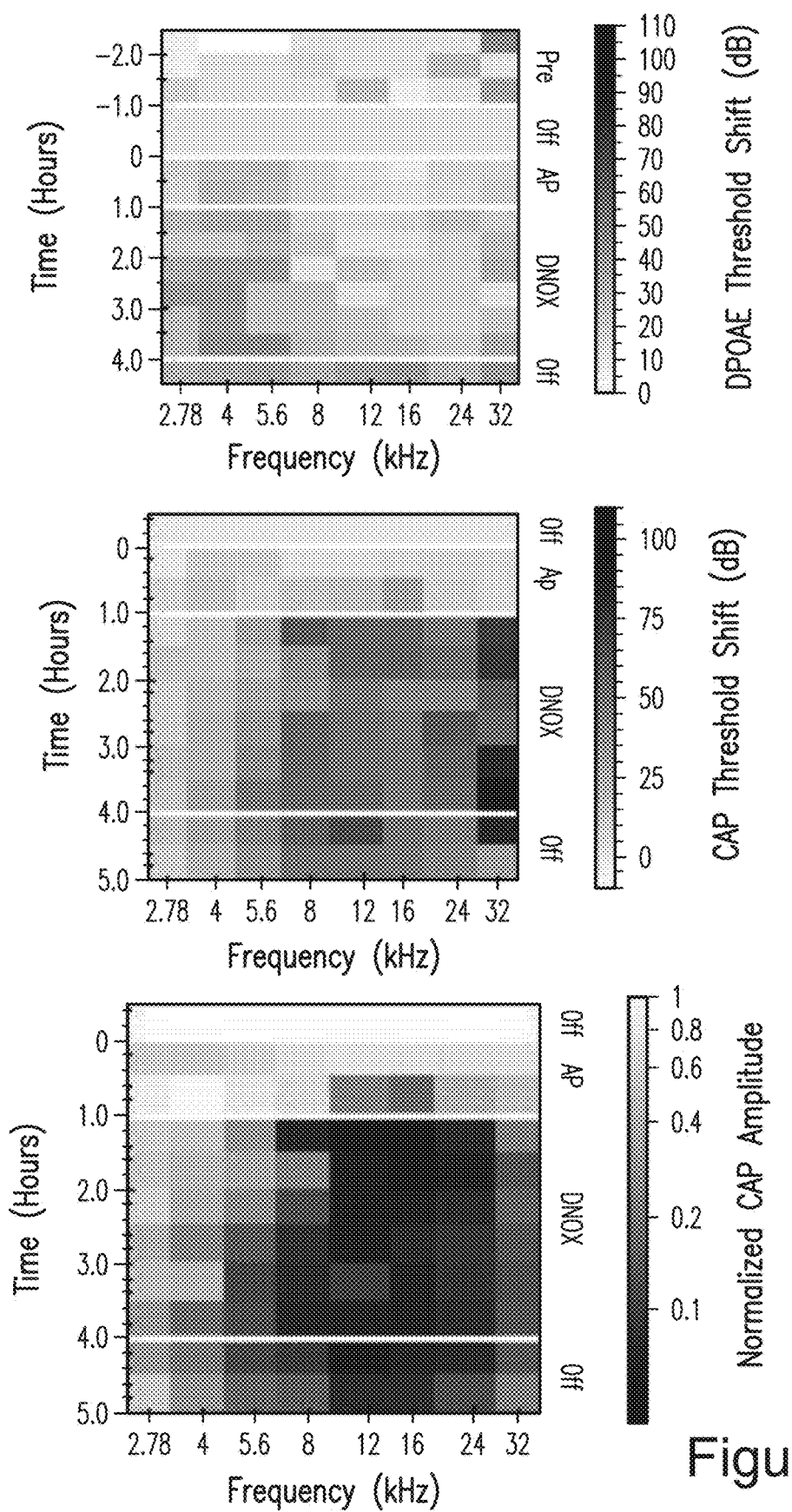

In the experiments described herein, drug concentration was not measured directly, but was inferred by mapping the drug-mediated CAP inhibition along the length of the ST to calculate drug concentrations at a given location. FIGS. 3(a)-3(b) show sample hearing measurements that serve as indicators of the response to DNQX. The observed reduction in CAP after initiation of drug delivery demonstrates the efficacy of the delivery process. The lack of alterations in DPOAE over time confirmed the safety of the procedure, indicating that there were no signs of mechanical damage or conductive hearing loss.

Figure 4A:
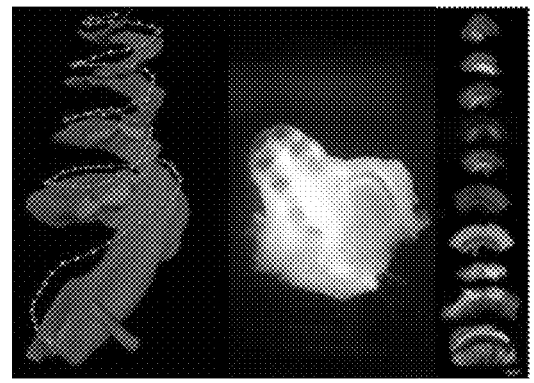
FIG. 4(a) shows a computer rendering of guinea pig scala tympani, showing injection site at the base of the cochlea (left), decalcified guinea pig cochlea (middle), and sections of guinea pig organ of Corti in whole mount preparation (right).
Figure 4B:
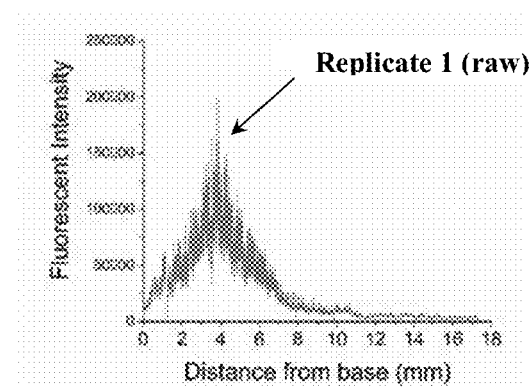
FIG. 4(b) shows an example of raw fluorescence intensity (FM 1-43 FX, a fixable derivative of the styryl dye FM 1-43) in the outer hair cells as a function of distance from the base of the cochlea.
Figure 4C:
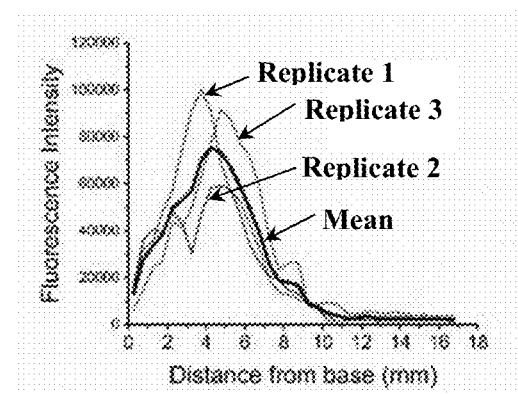
FIG. 4(c) shows the binned fluorescence intensity as a function of distance from the base of the cochlea showing similar staining pattern across 3 replicates.
Figure 5A:
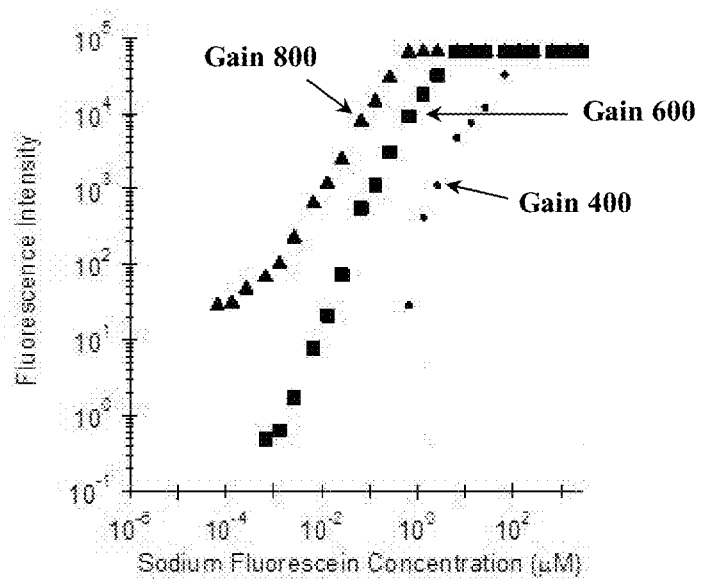
FIG. 5(a), FIG. 5(b), FIG. 5(c), and FIG. 5(d) show the process by which fluorescent tracer labelled drug molecules are evaluated for their safety and efficacy. The transport/concentration profiles of the drug are monitored via fluorescent signals (or alternatively by histology) using sectioning techniques and confocal microscopy evaluation following the delivery experiments described herein.
Figure 5B:
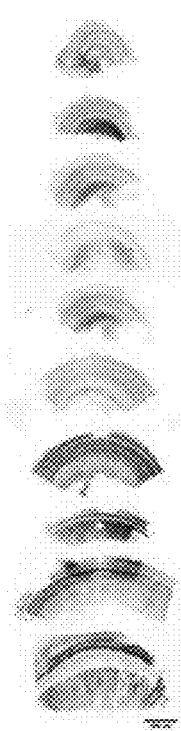
Figure 5C:
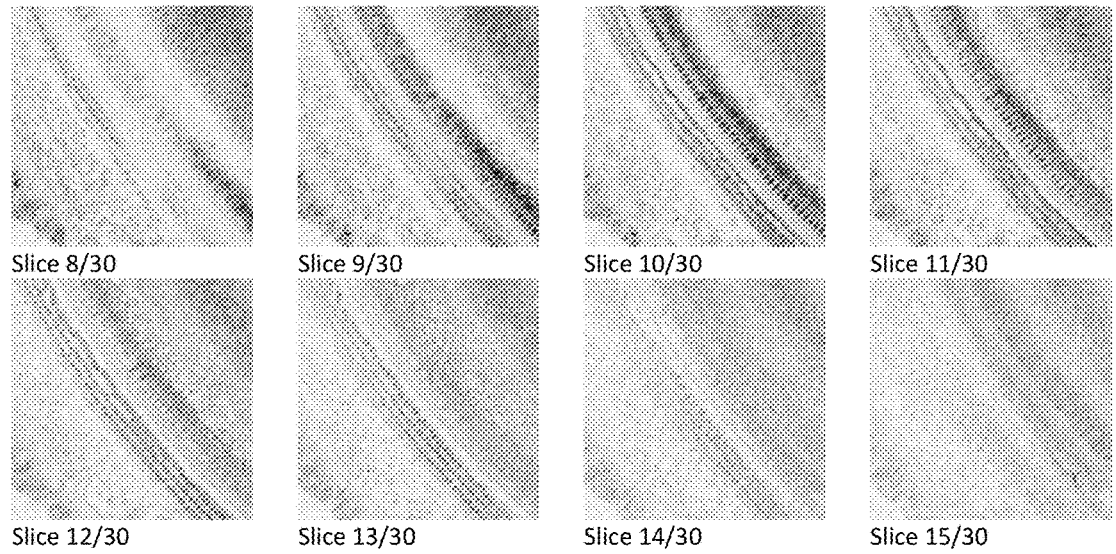
Figure 5D:
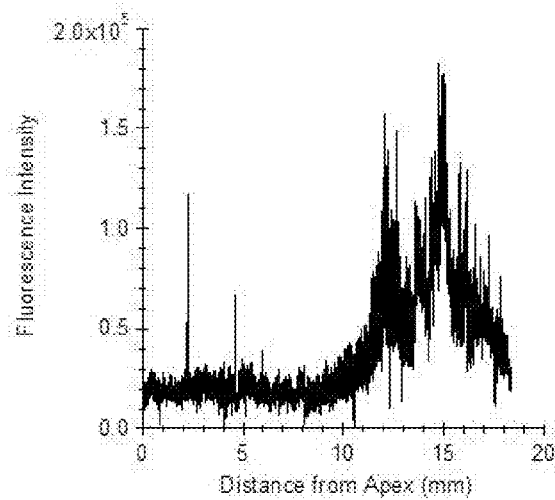

To visualize drug distribution within intracochlear structures post injection, FM 1-43 FX tracer was administered in solution (artificial perilymph) to the base of the cochlea following a cochleostomy procedure. FIG. 4(b) shows an example of raw fluorescence intensity (FM 1-43 FX) in the outer hair cells as a function of distance from the base of the cochlea. FIG. 4(c) shows the binned fluorescence intensity as a function of distance from the base of the cochlea showing similar staining pattern across 3 replicates.

FIGS. 5(a)-5(d) show the histopathologic assessment of hearing structures using fluorescent tracer compounds such as FM-143. Fluorescent tracer compounds were infused in solution (artificial perilymph) via a cochleostomy and were visualized using confocal microscopy. An estimated concentration gradient and profile was generated for each of the fluorescent tracer compounds. The results of these histopathological studies demonstrate the presence of a drug or tracer compound at various locations in the cochlea via fluorescent signals, and are useful for evaluating the histological effects on cells, tissues and hearing structures.

This Example demonstrates that the methods of the present technology are useful for delivering drugs into the cochlea via the perilymphatic fluid and for monitoring the histological effects on cochlear cells, tissues and hearing structures in a subject.

Example 3

Drug Delivery Methods of the Present Technology are Useful for Treating Auditory Disease and/or Hearing Loss This Example demonstrates that the methods of the present technology are useful for the treatment of auditory disease and/or hearing loss in a subject in need thereof.

Hydrogel formulations will be administered to the cochlea of a mammalian subject with hearing loss by injecting hydrogel precursors containing an inner ear therapeutic compound through the round window membrane or via a cochleostomy (fenestration) of the bone of the cochlea or semicircular canals. Aqueous hydrogel precursor solutions are Newtonian fluids with dynamic viscosity between $8.90 \times 10^{-4}$ Pa and $10^{-3}$ Pa, and may or may not contain fluorescent tracer compounds. Microfluidic tubing or a high-gauge needle is used to infuse the hydrogel precursors at a rate between 1 nL/min and 100 µL/min. The total volume of hydrogel precursors injected can vary between 1 nL and 100 µL. Chemical crosslinking of hydrogel precursor solutions will result in hydrogels with an elastic modulus between 1 and 1,000 kPa. Hydrogels will degrade by ester or amide hydrolysis, with gel residence time between 1 hour and 12 months. Hearing threshold elevations induced by gel formation are expected to be <40 dB. Functional assessment of hearing will include DPOAE, ABR, and CAP measurements. Histopathology will be assessed by visualizing the distribution of the fluorescent tracer compounds via confocal microscopy.

It is anticipated that the treated subjects will show signs of histological improvement in cochlear cells, tissues and hearing structures, and/or reversal or amelioration of hearing loss compared to untreated subjects with hearing loss. Accordingly, the methods disclosed herein are useful for the treatment of auditory disease and/or hearing loss in a subject in need thereof.

Equivalents

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All patents, patent applications, provisional applications, and publications referred to or cited herein are incorporated by reference in their entirety, including all figures and tables, to the extent they are not inconsistent with the explicit teachings of this specification.

The invention claimed is:

1. A method for treating an inner ear auditory disease in a subject in need thereof comprising administering an effective amount of a first pack composition and an effective amount of a second pack composition to the subject, wherein
   (a) the first pack composition comprises about 10 wt. % to about 50 wt. % by weight of the first pack composition of a PEG thiol, a PEG thiol-ester, or a mixture thereof; and water;
   (b) the second pack composition comprises about 10 wt. % to about 50 wt. % by weight of the second pack composition of a PEG Michael acceptor; and water; and
   (c) the first pack composition or the second pack composition further comprises at least one inner ear-specific therapeutic agent,
   wherein the first pack composition and the second pack composition are administered through a cannula that penetrates the round window membrane of the subject; wherein the PEG thiol, PEG thiol-ester, or mixture thereof comprises a multi-arm PEG thiol, a multi-arm PEG thiol-ester, or a mixture thereof; and wherein the first pack composition and the second pack composition forms a hydrogel network in vivo.

2. A method for treating an inner ear auditory disease in a subject in need thereof comprising administering an effective amount of a first pack composition and an effective amount of a second pack composition to the subject, wherein
   (a) the first pack composition comprises about 10 wt. % to about 50 wt. % by weight of the first pack composition of PEG thiol, a PEG thiol-ester, or a mixture thereof; and water;
   (b) the second pack composition comprises about 10 wt. % to about 50 wt. % by weight of the second pack composition of a PEG Michael acceptor; and water; and
   (c) the first pack composition or the second pack composition further comprises at least one inner ear-specific therapeutic agent,
   wherein the first pack composition and the second pack composition are administered through a cannula that accesses a cochleostomy site or a canalostomy site in the inner ear of the subject; wherein the PEG thiol, PEG thiol-ester, or mixture thereof comprises a multi-arm PEG thiol, a multi-arm PEG thiol-ester, or a mixture thereof; and wherein the first pack composition and the second pack composition forms a hydrogel network in vivo.

3. The method of claim 2, wherein the cochleostomy site is located within the cochlear bone of the subject.

4. The method of claim 2, wherein the canalostomy site is located within the semicircular canals of the subject.

5. The method of any one of claims 2-4, further comprising resealing the cannula with sodium hyaluronate, a muscle graft, a fat graft, or a fascia graft.

6. The method of any one of claims 1-4, wherein a microfluidic tubing or a high-gauge needle is used to infuse the first pack composition and the second pack composition through the cannula.

7. The method of any one of claims 1-4, wherein the first pack composition and the second pack composition are administered into a fluid-filled cochlear tube selected from the group consisting of scala tympani (ST), scala vestibuli, and scala media.

8. The method of any one of claims 1-4, wherein the at least one inner ear-specific therapeutic agent comprises a corticosteroid, an aminoglycoside, a free radical scavenger agent, a small peptide therapeutic, a gene therapy related agent, or a combination of any two or more thereof.

9. The method of any one of claims 1-4, wherein the at least one inner ear-specific therapeutic agent comprises ciprofloxacin, gacyclidine, a γ-secretase inhibitor, dexamethasone, hydrocortisone, methylprednisolone, prednisolone, gentamicin, amikacin, streptomycin, neomycin, tobramycin, N-acetylcysteine (NAC), methionine, tocopherol, vitamin E, ebselen, tiopronin, organic thiophosphate, copper compounds, an inhibitor for glycogen synthase kinase-3 beta (GSK3β), valproic acid, a TGF-β inhibitor, epidermal growth factor, basic fibroblast growth factor, insulin like growth factor 1, neurotrophin-3 (NT-3), an agonist for the GDNF receptor, brain derived neurotrophic factor, a lipid vector, a viral vector, a non-viral vector, a polyplex, a liposome, a microsome, a polymersome, a lioplex, an oligonucleotide, naked DNA, small RNA, CRISPR-Cas9, or a combination of any two or more thereof.

10. The method of any one of claims 1-4, wherein the first pack composition and the second pack composition are administered simultaneously or sequentially.

11. The method of any one of claims 1-4, wherein the subject is human.

12. The method of any one of claims 1-4, wherein the first pack composition and the second pack composition form a hydrogel having an elastic modulus between 1 and 1,000 kPa.

13. The method of any one of claims 1-4, wherein the first pack composition or the second pack composition further comprises a fluorescent tracer compound.

14. The method of claim 13, wherein the fluorescent tracer compound is selected from the group consisting of FM 1-43 FX, GTTR, Phalloidin, Hoechst, Mitotracker, Q-tracker, and CF SE.

15. The method of any one of claims 1-4, wherein the auditory disease is selected from the group consisting of sensorineural hearing loss, noise-induced hearing loss, sudden sensorineural hearing loss, autoimmune inner ear disease, tinnitus, cisplatin ototoxicity, radiation-induced ototoxicity, Meniere's disease, and cranial nerve schwannoma.

16. The method of any one of claims 1-4, wherein administration of the first pack composition and the second pack composition results in an increase in survival and/or regeneration of inner hair cells or outer hair cells.

17. The method of any one of claims 1-4, wherein administration of the first pack composition and the second pack composition results in an improvement of one or more electrophysiological parameters selected from the group consisting of ABR, CAP, hearing thresholds, and DPOAE relative to that observed in an untreated control subject having auditory disease.

18. The method of any one of claims 1-4, wherein the first pack composition and the second pack composition are administered as a single injection or multiple injections.

* * * * *